US007139675B2

(12) United States Patent  
Banks et al.

(10) Patent No.: US 7,139,675 B2
(45) Date of Patent: Nov. 21, 2006

(54) APPARATUS AND METHOD FOR PROBABILISTIC POPULATION SIZE AND OVERLAP DETERMINATION, REMOTE PROCESSING OF PRIVATE DATA AND PROBABILISTIC POPULATION SIZE AND OVERLAP DETERMINATION FOR THREE OR MORE DATA SETS

(75) Inventors: Steven M. Banks, Berne, NY (US); John A. Pandiani, Bristol, VT (US)

(73) Assignee: The Bristol Observatory, Ltd, Bristol, VT (US)

( * ) Notice: Subject to any disclaimer, the term of this patent is extended or adjusted under 35 U.S.C. 154(b) by 172 days.

(21) Appl. No.: 10/234,184

(22) Filed: Sep. 5, 2002

(65) Prior Publication Data

US 2003/0101028 A1   May 29, 2003

Related U.S. Application Data

(63) Continuation-in-part of application No. 08/795,706, filed on Feb. 4, 1997, now Pat. No. 6,470,298.

(51) Int. Cl.
G06F 15/00 (2006.01)

(52) U.S. Cl. .......................................... 702/181; 707/3
(58) Field of Classification Search ................ 702/179, 702/181; 705/3, 7, 10, 14; 707/3, 10, 101–102
See application file for complete search history.

(56) References Cited

U.S. PATENT DOCUMENTS

| 5,187,673 | A |   | 2/1993 | Carver, Jr. et al. |
| 5,539,752 | A |   | 7/1996 | Berezin et al. |
| 5,610,383 | A | * | 3/1997 | Chumbley ................ 235/386 |
| 5,634,049 | A | * | 5/1997 | Pitkin ...................... 707/102 |
| 5,659,731 | A |   | 8/1997 | Gustafson |
| 6,056,690 | A |   | 5/2000 | Roberts |
| 6,059,724 | A |   | 5/2000 | Campell et al. |
| 6,360,184 | B1|   | 3/2002 | Jacquez |
| 6,566,053 | B1| * | 5/2003 | Perucho et al. ............ 435/6 |

(Continued)

OTHER PUBLICATIONS

U.S. Appl. No. 08/795,706, filed Feb. 4, 1997, Steven M. Banks et al., Bristol Observatory, LTD.

(Continued)

Primary Examiner—Marc S. Hoff
Assistant Examiner—Mary Catherine Baran
(74) Attorney, Agent, or Firm—Staas & Halsey LLP

(57) ABSTRACT

The invention determines the population size and population overlap in data containing records on the unique entities without unique identifiers for the unique entities and having at least one common type of information with a known distribution of finite expectation by decomposing probabilistic calculations. The computer determines population overlap of unique entities between the data sets by subtracting a probabilistic incremental number of unique entities needed for a larger total number of values of the information with the known distribution from the data sets. The invention can also maintain the security of private data by allowing a remote computer where the original data is stored to download diagnostic and aggregation procedures from another computer over a network. The remote computer performs the functions on the data and forwards the results to the estimate processor computer over the network. The estimate processor determines population size and overlap from aggregate results and forwards this information back to the remote computer over the network. The invention also determines the overlap of three or more data sets by concatenating all combinations of the data sets and determining estimates for all subsets of the combinations of the data sets. The operations involve the cancellation of equivalent terms that have opposite signs.

3 Claims, 12 Drawing Sheets

U.S. PATENT DOCUMENTS

2001/0049620 A1 12/2001 Blasko

OTHER PUBLICATIONS

Feller, William, "An Introduction to Probability Theory and Its Applications", vol. 1, Second Edition, John Wiley & Sons, New York, (1957) pp. 210-211 and 224.

Abeni D.A., Brancato, G., and Perucci, C.A. "Capture-Recapture to Estimate the Size of the Population with Human Immunodeficiency Virus Type 1 Infection", Epidemiology, vol. 5, No. 4 (Jul. 1994), pp. 410-414.

Larsen, S.O. "Estimation of the Number of People in a Register from the Number of Birth dates", Statistics in Medicine, vol. 13 (1994) pp. 177-183.

Nomura, "Effective Size of Selected Populations with Overlapping Generations", J. Anim. Breed. Genet., 1996.

Atlas et al., "Comparative-Evaluation of Two Superior Stopping Rules for Hierarchical Cluster-Analysis", Psychometrical, 1994.

Houle et al., "Project on Matching Census 1986 Database and Manitoba Health Care Files: Private Households Component", Mar. 1996.

Bell et al., "Matching Records in a National Medical patient Index", Sep. 2001.

Pandiani JA, Banks SM, Schacht LM, "Personal Privacy vs. Public Accountability: A Technological Solution to an Ethical Dilemma", Journal of Behavioral Health Services and Research, Nov. 1998;25(4):456-63.

Hendricks E, Hayden T, Novik JD, "Your Right to Privacy: A Basic Guide to Legal Rights in an Information Society", Carbondale, IL: Southern Illinois University Press, 1990.

National Center for Health Statistics, NCHS Staff Manual on Confidentiality, Hyattsville MD: Department of Health and Human Services; 1984.

Stroul, B.A. & Friedman, R.M, (1986), "A system of care for children and youth with severe emotional disturbances (rev. ed.)", Washington DC: Georgetown University Child Development Center, CASSP Technical Assistance Center.

Whitehead, A.M., & Russell, B. (1927), "Principia Mathematica", vol. 1, 2nd Ed. Cambridge, University Press, pp. 211-212.

Donaldson MS, Lohr KN, (1994) "Health Data in the Information Age: Use Disclosure and Privacy", Institute of Medicine, Washington DC: National Academy Press, pp. 51.

Standards for Privacy of Individually Identifiable Health Information, Final Rule (45CFR 164).

Secretary's Advisory Committee on Automated Personal Data Systems, Records, Computers, and Rights of Citizens: Report of Advisory Committee on Automated Personal Data Systems US Department of Health, Education, and Welfare, Washington DC. U.S. Government Printing Office, 1973.

Pandiani, et al., Using Incarceration Rates to measure Mental Health Program Performance, Aug. 1998, pp. 300-311.

Rosenheck, et al., Bed Closures and Incarceration Rates Among Users of Veterans Affairs Mental Health Services, Oct. 2000, vol. 51 No. 10 pp. 1282-1287.

Rosenheck, et al. Does Closing Inpatient Beds in One Public Mental Health System Result in Increased Use of Hospital Services in Other Systems?, 2000, 183-189.

Banks, et al. Probabilistic population estimate of the size and overlap of data sets based on date of birth, 2001, pp. 1421-1430.

Pandiani, et al., Elevated Risk Of Being Charged With A Crime For People With A Severe And Persistent Mental Illness, Fall 2000, vol. 2, No. 2, pp. 19-36.

Pandiani, et al., A Global Measure of Access To Mental Health Services For A Managed Care Environment, Summer of 1997, pp. 268-277.

Banks et al., Age and Mortality Among White Male Problem Drinkers, Aug. 7, 1999, pp. 1249-1254, Carfax Publishing, Taylor & Francis Ltd.

Pandiani, J.A., Banks, S.M., & Schacht, L.S., (1999) "Caseload Segregation/Integration: A Measure of Shared Responsibility for Children and Adolescents", 7 (2) pp. 66-71 Journal of Emotional and Behavioral Disorders.

Pandiani, et al., (2001) Caseload Segregation/Integration and Treatment Outcomes for Children and Adolescents, Winter 2001, pp. 232-238, Journal of Emotional And Behavioral Disorders. (Abstract).

Banks et al., "Approaches to Risk-Adjusting Outcome Measures Applied to Criminal Justice Involvement after Community Service", 2001.

Banks et al., Using Existing Databases to Measure Treatment Outcomes, Mario Hernandez & Sharon Hodges (Eds.), Developing Outcomes Strategies in Children's Mental Health, by Paul H. Brookes Publishing Co., Inc.

Pandiani, et al. "Measuring Access to Mental Health Care: A Multi-Indicator Approach to Program Evaluation", May 14, 2002 pp. 1-16, Evaluation and Program Planning.

Pandiani, et al. "Morality of Mental Health Service Recipients in Vermont and Oklahoma" Aug. 2002, vol. 53, No. 8, pp. 1025-1027, Psychiatric Services.

Banks, et al. "Utilization of Local Jails and General Hospitals by State Psychiatric Center Patients", Nov. 2000, pp. 454-459, The Journal of Behavior Health Servicces & Research.

John A. Pandiani, "A Virtual MIS For Child and Adolescent Systems of Care", 2000, p. 2, Vermont Mental Health Performance Indicator Project.

Banks, et al., "The Use of State and General Hospitals for Inpatient Psychiatric Care", Mar. 1998, pp. 448-451, vol. 88. No. 3, American Journal of Public Health.

Pandiani, et al., "Consumer Satisfaction and Incarceration After Treatment", Nov. 2001, pp. 145-155, vol. 29, No. 2, Administration and Policy in Mental Health.

Banks, et al., "The Use of State and General Hospitals for Inpatient Psychiatric Care", Mar. 1998, pp. 448-451, vol. 88, No. 3, American Journal of Public Health.

Pandiani, et al. Mortality of Mental Health Service Recipients in Vermont and Oklahoma, Aug. 2002, pp. 1025-1027, vol. 53, No. 8, Psychiatric Services.

Michelle Woodbridge, et al., Interagency MIS: Higher Order Connection, Spring 2001, Georgetown University National Technical Assistance Center for Children's Mental Health.

United States General Accounting Office, Record Linkage And Privacy: Issues in Creating New Federal Research and Statistical Information, Apr. 2001, pp. 1-167.

Research Community and Mental Health in Fischer, W (ED.) Research in Community and Mental Health in press, Elsevier Science.

Pandiani, et al., Elevated Risk of Arrest for Veteran's Administration Behavioral Health Service Recipients in Four Florida Countries, Under Review. (Abstract).

Pandiani, et al., Educational test Scores for Measuring Children's Mental Health Programs Performance, Journal of Behavioral Health Services. (Abstract).

Pandiani, et al., Atyical Anti-Psychotic Medications and Criminal Justice, The American Journal. (Abstract).

Banks, et al., A Methodology for Probabilistically Estimating Caseload Size and Overlap, Jan. 1999, The Evaluation Center @HSRI.

* cited by examiner

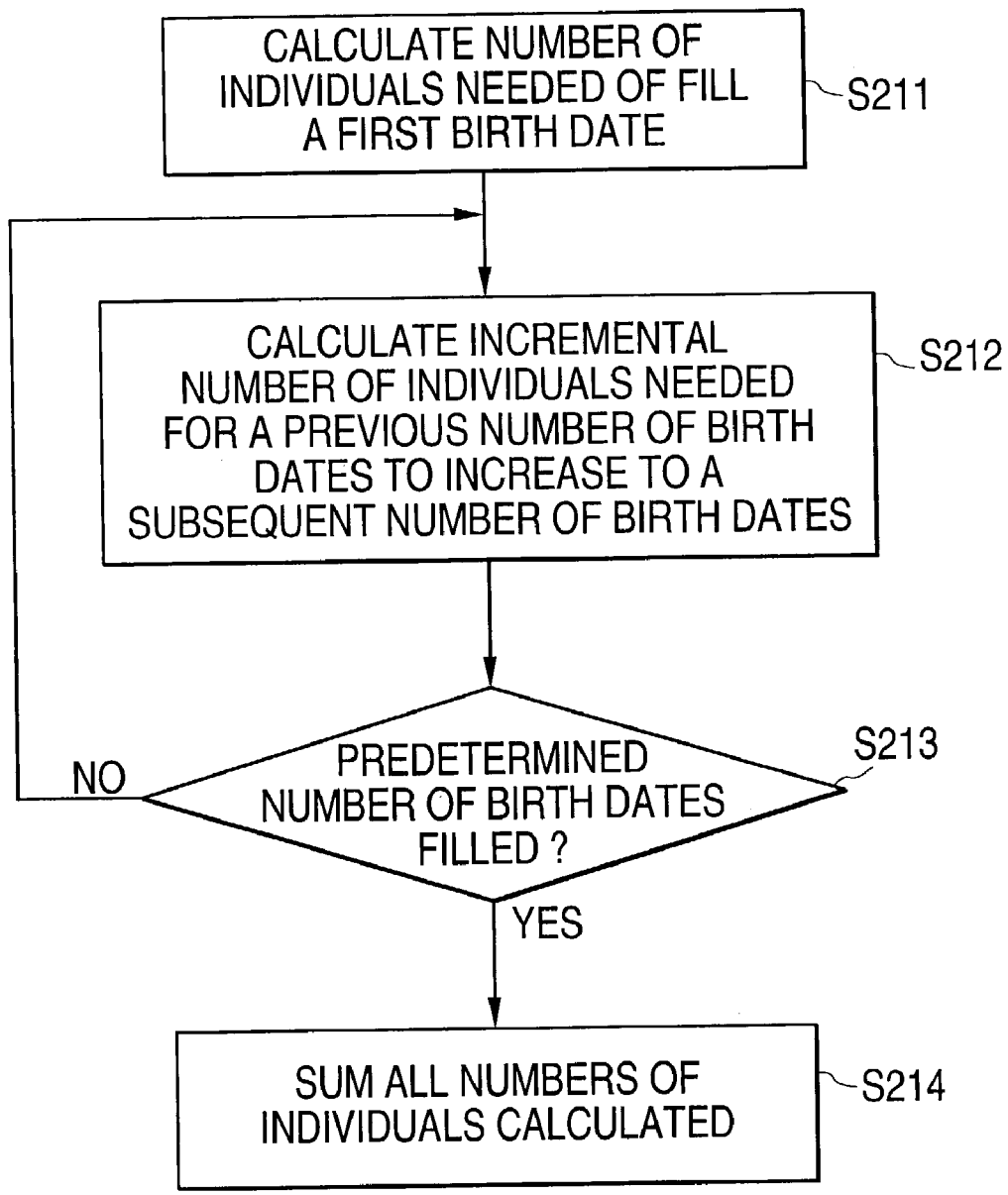

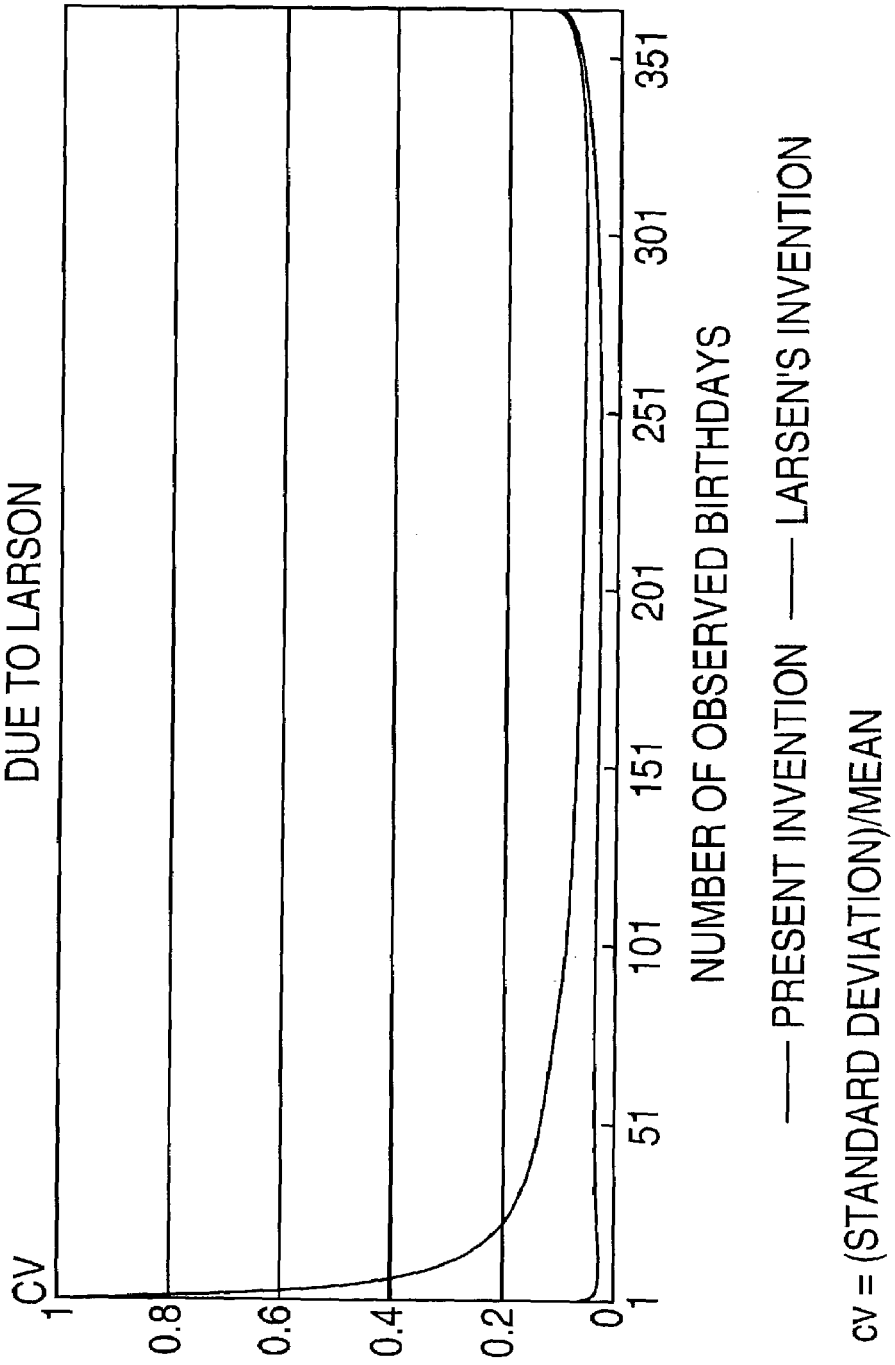

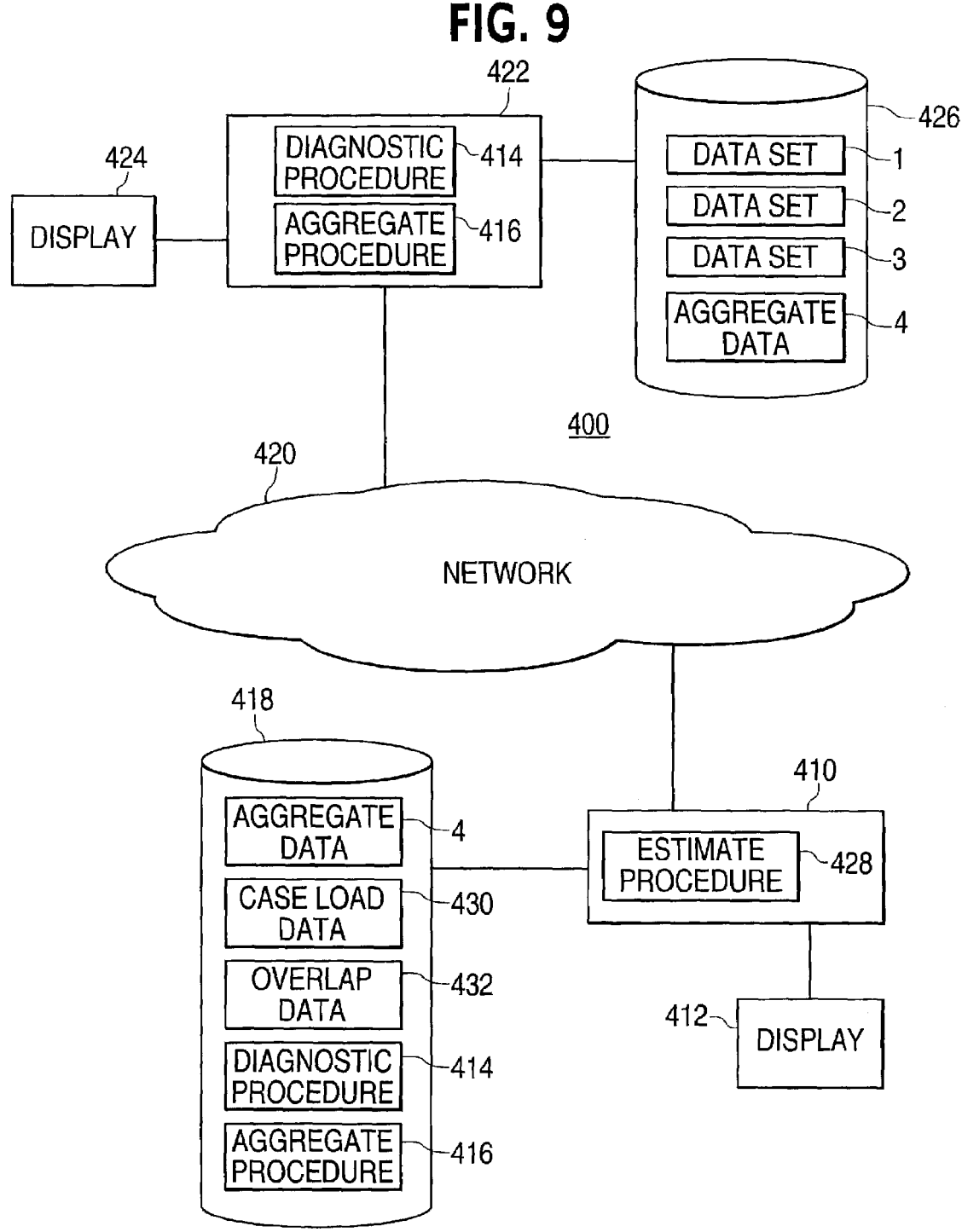

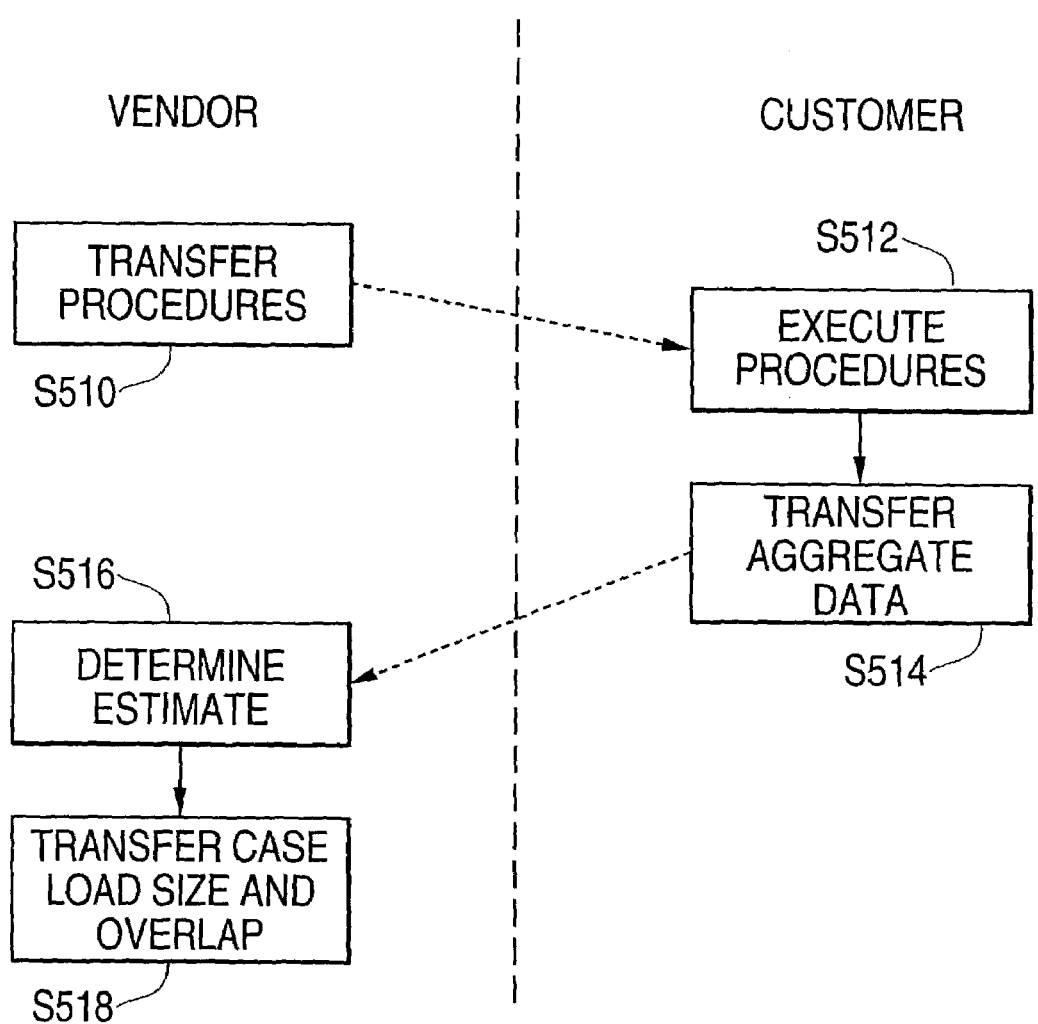

HYPOTHETICAL 3-WAY OVERLAP
MENTAL HEALTH (MH), SUBSTANCE ABUSE (SA),
AND CRIMINAL JUSTICE (CJ) CASELOADS

APPARATUS AND METHOD FOR PROBABILISTIC POPULATION SIZE AND OVERLAP DETERMINATION, REMOTE PROCESSING OF PRIVATE DATA AND PROBABILISTIC POPULATION SIZE AND OVERLAP DETERMINATION FOR THREE OR MORE DATA SETS

CROSS-REFERENCE TO RELATED APPLICATIONS

This application is a continuation-in-part of and claims priority to U.S. application entitled Apparatus And Method For Probabilistic Population Size And Overlap Determination having Ser. No. 08/795,706, by Banks and Pandiani, filed Feb. 4, 1997 now U.S. Pat. No. 6,470,298 and incorporated by reference herein.

REFERENCE TO COMPUTER PROGRAM LISTING, COMPACT DISK APPENDIX

A compact disc is included herewith and incorporated by reference herein having thereon a computer program listing appendix (Appendix I) in the ASCII uncompressed tex format with ASCII carriage return, ASCII line feed and all control codes defined in ASCII, having computer compatibility with IBM PC/XT/AT or compatibles, having operating system compatibility with MS-Windows and including file Appendix I of 54.6 kilobytes created on Sep. 4, 2002.

BACKGROUND OF THE INVENTION

1. Field of the Invention

The present invention relates to an apparatus and method for determining population size and overlap within information sources. More specifically, the present invention relates to a statistical technique for measuring population overlap in plural data sets without reliance on unique identifiers, and provides an alternative and superior method for determining population size using a technique that allows the holder of the information to summarize the features of the information, forward the summary to a processor which determines the overlap thereby enhancing the privacy of the original information.

2. Description of the Related Art

Government and private industry need to know the number of people who are involved in more than one institution, program, group, or activity, either concurrently or in sequence for purposes of management, monitoring, and evaluation.

The measurement of population overlap has been hampered by both the complexity of the social institutions and the lack of unique personal identifiers across existing data sets. Until now, the determination of the number of individuals shared across sub-populations has relied on one or more of three approaches to the problem: (1) the construction of detailed case registries (single data sets); (2) implementation of a true unique id system (e.g. National ID card) across multiple data sets; and (3) case by case matching of records from multiple data sets that describe the members and/or activities of various organizations and service sectors.

Traditionally, the problem of data set overlap has been most commonly approached by the development of case registries. The Gulf War Registry, designed to allow medical researchers to determine the prevalence and distribution of Gulf War Syndrome is one current example. The National Breast Cancer Registry is another. In the 1960s, a number of states established psychiatric case registries in order to determine the prevalence and distribution of mental illness. In every case the problem was the same. Existing fragmented information systems could not support the critical epidemiological functions of determining the relationship among existing data sets. There are three important shortcomings to this approach. First, the creation of case registries is a very expensive undertaking. Second, the completeness of a registry is always in question, especially when participation is voluntary. The incompleteness of the Gulf War Registry is notorious. Finally, because they necessarily include personal identifiers, the creation of case registries raises important issues about personal privacy and confidentiality of personal records.

The implementation of universal true unique personal identifier systems provides a second solution to the problem of determining the number of people involved in different subpopulations. While the implementation of such identification systems has been successfully accomplished for specific organizations (e.g. individual hospitals, correctional facilities, and insurance companies), these identification systems do not constitute the kind of universal identification systems that allow for analysis of membership overlap. In the United States, the social security number comes close to providing a universal identification system, but concerns about personal privacy severely limit the availability of these identifiers in settings not directly related to the social security system.

Case by case matching of records from multiple data sets based on the names of people or other identifiers that may be shared by more than one data set is a third approach to the problem. Case by case database integration on a patient specific basis has been utilized in a number of fields. From a practical point of view, this approach is has two major shortcomings. First, it is tedious, time consuming, and expensive. Second, it includes an unquantifiable degree of error. This approach also depends on personal identifiers, so concerns about privacy and confidentiality are likely to limit its utilization.

The problem of measuring the overlap between populations where no unique person identifier exists is related to the problem of measuring population size (the number of distinct individuals) without a unique person identifier. The problem of estimating population size may, in fact, be seen as a constituent part of the larger problem of estimating population overlap. In the past, the measurement of the number of people represented in a single data set that does not include a unique person identifier has relied on either of two statistical approaches. One statistical approach applies the capture-recapture sampling technique to the problem. This approach is illustrated by Abeni et al., "Capture-Recapture to Estimate the Size of the Population with Human Immunodeficiency Virus Type 1 Infection," *Epidemiology*, Volume 5 Number 4, July 1994 (pp. 410–414). The other statistical technique is based on a classical occupancy theory, as discussed by Feller, "An Introduction to Probability Theory and Its Applications," Volume 1, Second Edition, 1957. The classical occupancy theory is described on pages 210–211 and 224 of Feller's text. One implementation of the classical occupancy theory has been provided by Larsen, "Estimation of the Number of People in a Register from the Number of Birthdates," *Statistics in Medicine*, Volume 13, 1994 (pp. 177–183). The present invention uses a fundamentally different, and far superior, implementation of the classical occupancy theory.

The capture-recapture technique is, in essence, case by case matching of small samples of larger populations. It avoids the cost associated with complete case-by-case matching, but still raises issues of personal privacy and confidentiality because it relies on personal identifiers for a subset of the population. Capture-recapture was originally developed by ecologists to estimate the size of wildlife populations. In the simplest setting, a sample of wildlife is captured, tagged, and released. At a later time, a second sample is drawn and overlap with the first sample is determined. The sizes of the two samples and their overlap are used to statistically determine the size of the total population and the confidence interval associated with the estimate. In applications to human populations, capture-recapture draws samples from lists of members of subpopulations. Personal identifiers are used to measure overlap of the samples and statistical computations are used to determine the size of the overall population. The greatest shortcoming of the capture-recapture approach is the large confidence intervals associated with the measure. It is not unusual to find confidence intervals of 50% of the population parameter as illustrated by Abeni et al.

A statistical procedure that addresses the problem of estimating the size of a population without a unique personal identifier has been provided by Larsen's maximum likelihood estimate of the solution to the classical occupancy problem. Larsen applied his solution to the estimation of the number of people represented in an anonymous Chlamydia registry in one county in Denmark. His solution provides less precise estimates and contains greater error than the solution provided by the present invention. In addition, his solution does not address the population overlap problem.

In recent years, the proliferation of electronic data bases in conjunction with dramatic advances in data processing technology have led to increasing concern about threats to personal privacy and, more specifically, about the confidentiality of medical records. (See Secretary's Advisory Committee on Automated Personal Data Systems. Records, Computers, and Rights of Citizens: Report of the Advisory Committee on Automated Personal Data Systems, US Department of Health, Education, and Welfare. Washington D.C. U.S. Government Printing Office, 1973; Hendricks E, Hayden T, Novik J D. Your Right to Privacy: A Basic Guide to Legal Rights in an Information Society. Carbondale, Ill: Southern Illinois University Press, 1990; and Donaldson M S, Lohr K N. Health Data in the Information Age: Use Disclosure and Privacy. Institute of Medicine. Washington D.C.: National Academy Press; 1994. p 51.)

In 1996, the United States Congress passed the Health Insurance Portability and Accountability Act (PL 104–191) that requires the Secretary of Health and Human Services to promulgate federal regulations that protect the privacy of health information if congress had not enacted legislation in this area by August of 1999. In December 2000, Standards for Privacy of Individually Identifiable Health Information; Final Rule (45 CFR 164) were promulgated. (See Standards for Privacy of Individually Identifiable Health Information; Final Rule (45 CFR 164) were promulgated. UPDATE § 164.514 Other requirements relating to uses and disclosures of protected health information.) In this rule, section § 164.514 notes "Other requirements relating to uses and disclosures of protected health information" includes the requirement that: "(2)(i) The following identifiers of the individual or of relatives, employers, or household members of the individual, are removed: . . . (C) All elements of dates (except year) for dates directly related to an individual, including birth date . . . ".

The current debate regarding medical records privacy involves a classic confrontation of public and private goods. (See Pandiani J A, Banks S M, Schacht L M. Personal Privacy vs. Public Accountability: A Technological Solution to an Ethical Dilemma. Journal of Behavioral Health Services and Research. 1998 November;25(4):456–63.) Personal privacy is an important value in contemporary American society. Legislation in support of personal privacy and the confidentiality of medical records would be likely to receive widespread support if it did not have the potential to undermine another set of important national values. These values favor rational administration of public programs and the right of people to be able to make informed choices regarding their health care.

The Institute for Medicine offers a broad definition of personally identifiable information when it includes: " . . . items of information (e.g. the fact of a physician visit on a given day) that will allow identification of an individual when combined with other facts (e.g. zip code, date of birth, and gender)." (See Hendricks E, Hayden T, Novik J D. Your Right to Privacy: A Basic Guide to Legal Rights in an Information Society. Carbondale, Ill.: Southern Illinois University Press, 1990.)

The Public Health Service endorsed an even stricter definition of personally identifiable information when it promulgated guidelines that prohibited the release of data tapes that contain: " . . . any detailed information about the subject that could facilitate identification . . . (e.g., exact date of the subject's birth)." (See National Center for Health Statistics. NCHS Staff Manual on Confidentiality. Hyattsville Md.: Department of Health and Human Services; 1984.)

What is needed is an approach to determining overlap that enhances protection of the privacy of the original information.

Government and private industry also need to know the unduplicated number of individuals shared by more than two data sets. For instance, government agencies want to know if people served by both substance abuse and mental health agencies have better outcomes than people served by either alone. Relevant outcomes include levels of criminal justice involvement, employment, hospitalization, and mortality. Many government agencies and consumer advocates want to know about the degree of integration among multiple agencies, especially with regard to child serving agencies. Such measures address efficiency concern as well as concerns about he adequacy of care. (See Stroul, B. A. & Friedman, R. M. (1986). *A system of care for children and youth with severe emotional disturbances.* (rev. ed.). Washington D.C.: Georgetown University Child Development Center, CASSP Technical Assistance Center; and Pandiani, J. A., Banks, S. M., & Schacht, L. S.: (1999) Caseload Segregation/Integration: A Measure of Shared Responsibility for Children and Adolescents, Journal of Emotional and Behavioral Disorders 7(2)66–71.)

The difficulty of measuring the overlap between data sets tends to increase with the number of data sets involved. This is because multiple data sets are less likely to share person identifiers, state and federal regulations are more likely to limit access to one or more of the data sets because of privacy concerns.

What is needed is an approach that will allow the size and overlap in three or more data sets to be determined.

SUMMARY OF THE INVENTION

Accordingly, it is an aspect of the present invention to identify an accurate quantity of unique individuals (entities, objects, items, etc.) in a data source containing potentially multiple records pertaining to a particular individual.

It is a further aspect of the present invention to identify an accurate quantity of unique individuals (entities, objects, items, etc.) overlapping across multiple data sources that may contain multiple records pertaining to a particular individual within a single data source or within multiple data sources.

It is another aspect of the present invention to determine a more precise and smaller range of variance of the quantity of unique individuals (or items) at a specified confidence interval (e.g. 95%) in a single data source or overlapping across multiple data sources which contain potentially multiple records regarding a particular individual in a single data source and/or across multiple data sources.

It is also an aspect of the present invention to maintain the private information with the original data holder and provide to a data overlap processor that information necessary to determine the overlap.

It is an additional aspect of the present invention to determine the size and overlap of three or more data sets.

The above aspects are achieved by providing an apparatus and method for probabilistic population size determination. The apparatus and method uses a computer to probabilistically calculate the population size of unique entities in data, containing records on unique entities without unique identifiers for the unique entities and having at least one common type of information with a known distribution of finite expectation, using decomposed probabilistic calculations based on values of the information with the known distribution. The decomposed probabilistic calculations used in determining population size include calculating a first probabilistic number of unique entities needed to satisfy a first value of the information with the known distribution, successively calculating a probabilistic incremental number of unique entities needed for a previous value of the information with the known distribution to increase to a subsequent value of the information with the known distribution, until the probabilistic number of unique entities needed to increase to a predetermined value of the information with the known distribution is calculated, and summing the first probabilistic number of unique entities and the probabilistic incremental numbers of unique entities.

The aspects are also achieved by providing an apparatus and method for probabilistic population size and population overlap determination. Data is found in first and second data sets containing records on the unique entities without unique identifiers for the unique entities and having at least one common type of information with a known distribution of finite expectation. A computer combines the first and second data sets into a combined data set and probabilistically calculates the population size for the first and second data sets in a fashion similar to the apparatus and method discussed in the preceding paragraph. The population overlap of the unique entities between the first and second data sets is then determined by subtracting a probabilistic incremental number of unique entities needed for a larger total number of values of the information with the known distribution from either of the first and second data sets to increase to a total number of values of the information with the known distribution in the combined data set from a smaller of the population size of the first and second data sets.

The aspects are also achieved by providing an apparatus (and a corresponding method) for probabilistic determination of population size and overlap having a storage medium, a data preparation unit, a population size measurement unit, a population overlap measurement unit, and a total population information generator. The storage medium stores first and second data sets containing the records on individuals without unique identifiers for the individuals, and the records have information on gender and birth date for each individual. The data preparation unit subdivides the records in the first, second, and combined data sets into multiple gender/year of birth cohorts, and determines a total number of unique birth dates in the first, second, and combined data sets for each gender/year of birth cohort. The population size measurement unit probabilistically calculates the population size for the first and second data sets in each gender/year of birth cohort by calculating a first probabilistic number of individuals needed to fill one date of birth, successively calculating a probabilistic incremental number of individuals needed for a previous number of dates of birth to increase to a subsequent number of dates of birth, until the probabilistic number of unique entities needed to increase to the total number of unique dates of birth is calculated, and summing the first probabilistic number of individuals and the probabilistic incremental numbers of individuals. The population overlap measurement unit determines the population overlap of the individuals between the first and second data sets by subtracting a probabilistic incremental number of individuals needed for a larger total number of unique birth dates from either of the first and second data sets to increase to a total number of unique birth dates in the combined data set from a smaller of the population size of the first and second data sets. The total population information generator calculates a total population size and a total population overlap by summing the population size of the first and second data sets and the population overlap across the multiple gender/year of birth cohorts.

The aspects are further achieved by providing a data preparation unit that performs diagnosis to identify discrepancies between the observed value and the maximum expected value of the information with the known distribution and to generate a warning or recommend solutions to overcome the discrepancy.

The population size measurement unit also calculates a population size variance corresponding to the population size determined for the first and second data sets for each gender/year of birth cohort. The population overlap measurement unit also calculates a variance corresponding to the probabilistic incremental number of individuals needed for the larger total number of unique birth dates from either of the first and second data sets to increase to the total number of unique birth dates in the combined data set, and calculates lower and upper population overlap variance values corresponding to the population overlap for each gender/year of birth cohort. The total population information generator calculates a total population size variance by summing the population size variance for the first and second data sets across the multiple gender/year of birth cohorts, and calculates total lower and upper population overlap variance values by summing the lower and upper population overlap variance values across the multiple gender/year of birth cohorts.

The population overlap measurement unit also calculates a ninety-five percent confidence interval for the population overlap for each gender/year of birth cohort and the total population information generator calculates a ninety-five percent confidence interval for the total population overlap based on the total lower and upper population overlap variance values and eliminating impossible ranges in variance.

The aspects of the present invention are further achieved by providing an apparatus and method for probabilistic population overlap determination when the population size is known for a first and second data set containing unique entities identified by unique identifiers, but where the type of unique identifiers in the first data set are different from the type of unique identifiers used in the second data set. A storage medium stores first and second data sets containing records on the unique entities with first unique identifiers for the unique entities in the first data set different from second unique identifiers for the unique entities in the second data set, and having at least one common type of information with a known distribution of finite expectation. A computer combines the first and second data sets into a combined data set and determines the population overlap of the unique entities between the first and second data sets by subtracting a probabilistic incremental number of unique entities needed for a larger total number of values of the information with the known distribution from either of the first and second data sets to increase to a total number of values of the information with the known distribution in the combined data set from a smaller of the population size of the first and second data sets.

The aspects of the invention are also achieved by providing an apparatus and method that allows a remote computer where the original data is stored to download diagnostic and aggregation functions from another computer. The remote computer performs diagnostic and aggregation functions on the original data and forwards the results to an estimate processor computer. The estimate processor determines population size and overlap from the aggregate results and forwards this information back to the remote computer.

The aspects are additionally achieved by providing an apparatus and method for determining the overlap of three or more data sets by concatenating all combinations of the data sets and determining estimates for all subsets of the combinations of the data sets.

BRIEF DESCRIPTION OF THE DRAWINGS

These and other objects and advantages of the invention will become apparent and more readily appreciated from the following description of the preferred embodiments, taken in conjunction with the accompanying drawings.

FIG. 5 is a flow chart describing detailed operations for the measurement of population size for original data sets operation S210 of FIG. 4.

FIG. 8 is a comparison chart between the coefficients of variation between determinations produced by the present invention and those produced by Larsen.

FIG. 9 depicts distributed processing of the present invention.

FIG. 10 illustrates operations of the distributed processing.

DETAILED DESCRIPTION OF THE PREFERRED EMBODIMENTS

Figure 1:
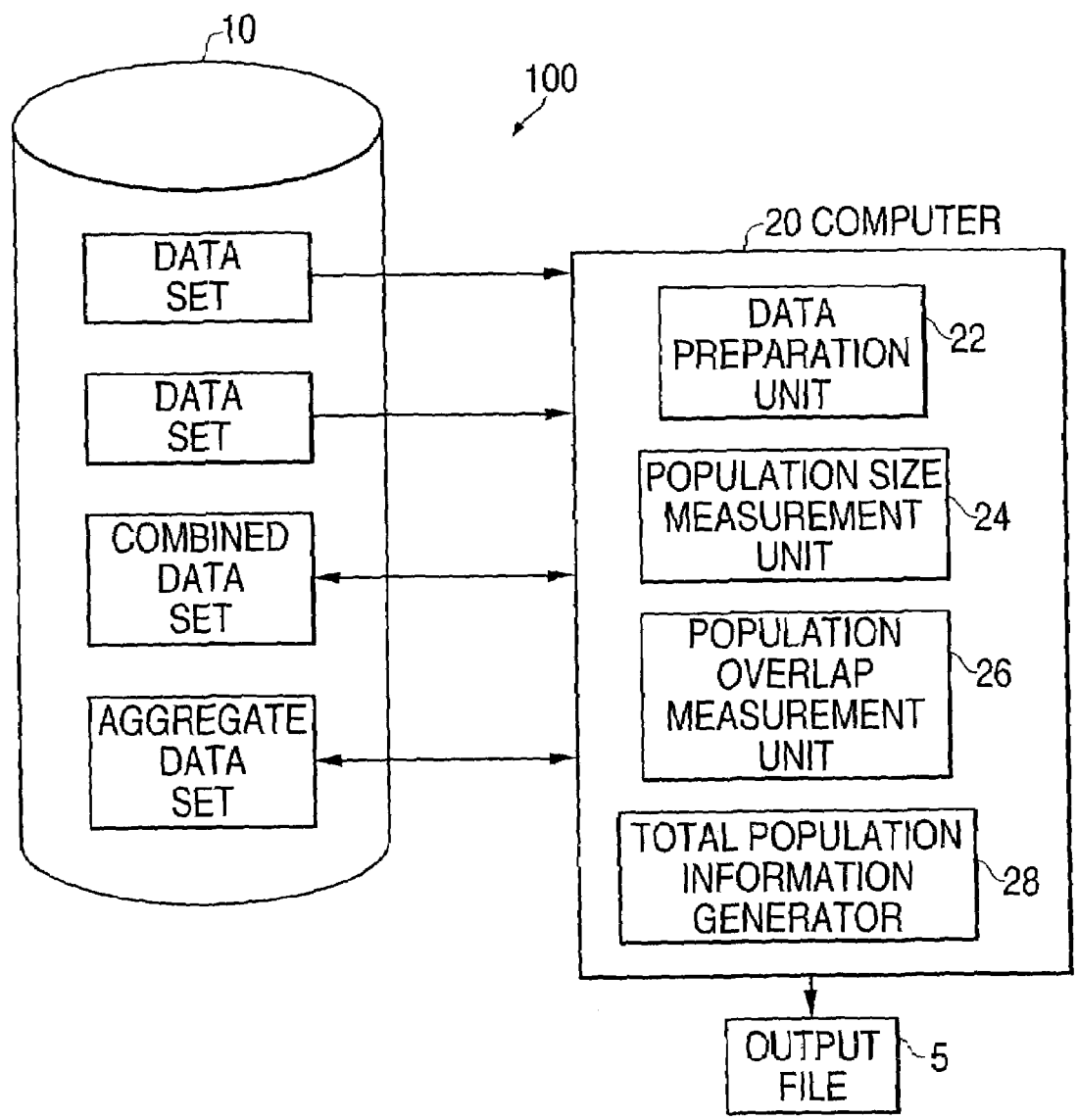
FIG. 1 is a block diagram of a population size and overlap determination apparatus according to a preferred embodiment of the present invention.

The paragraphs that follow will provide a detailed description of the preferred embodiments of the invention for determining the size and overlap of human populations doing so in a distributed processing system and doing so with more than two data sets, and a simple example of the application of the invention to non-human populations. These paragraphs will also include a discussion of the general mathematical theory underlying the invention, and distinguish the solution to the population size problem offered by this invention from other solutions on both theoretical/mathematical and empirical grounds. Since mathematical solutions to the population overlap problem that do not require unique individual identifiers are not evident in the literature, the mathematics of this solution will be discussed without contrast to other solutions.

In the classical coupon collector problem, the solution to the problem answers the question "How many baseball cards must a collector collect to obtain a complete set of cards, when the probability of every card being in a given bubble gum package is known?". Larsen, for instance, provided a solution to this classical occupancy problem. However, Larsen solves the classical occupancy problem using maximum likelihood estimation techniques. In particular, Larsen approximated the classical occupancy theory using the Poisson distribution. By using the approximation, Larsen was able to estimate the size of a population and its variance.

In fundamental contrast to Larsen, the present invention solves the classical occupancy problem using random variable decomposition techniques, without resort to approximation. The present invention is able to provide a determination of population size and variance that is based on a different probabilistic method. In particular, the present invention builds upon the classical occupancy theory, but provides an operationalization of classical occupancy theory that is fundamentally different from the operationalization provided by Larsen. First, the present invention decomposes the problem into a set of constituent problems before applying a mathematical model, while Larsen's formulation begins with the application of his mathematical model. Second, the present invention allows for the selection of a mathematical model that is appropriate to the specific distribution under examination, while the mathematical model used in Larsen's formulation only applies when the characteristic is uniformly distributed.

Larsen's solution to the coupon collector problem begins with a mathematical approximation in the first operation of the solution that requires that the distribution of the known characteristic be uniform. Where "I" is the number of observed dates of birth in a gender/year of birth cohort and where $P_j$ is the population estimate for each gender/year of birth subset "j", Larsen's technique would determine the number of individuals to be $$P_j(l) = 365 \times \log\left(\frac{365}{365-l}\right) \quad (1)$$

and the variance $\sigma^2(P_j(l))$ to be $$\sigma^2(P_j(l)) = \frac{(l \times 365)}{(365-l)} \quad (2)$$

The solution to the coupon collector problem used in the present invention begins with a decomposition of the problem that does not involve mathematical approximation. This decomposition involves breaking down the larger question into a series of smaller questions for which the mathematical solution is known. In a preferred embodiment of the present invention, the present invention applies this decomposition to the determination of the number of unique individuals (persons or other entities) represented in a data set that does not include a unique individual identifier. Using decomposition, the total number of individuals needed to fill a prespecified number of categories (of an attribute having a known distribution of finite expectation) is equivalent to the number of individuals needed to fill one category, plus the number needed to fill a second category once the first is full, plus the number necessary to fill a third once the second is filled, etc., until the prespecified number of categories is filled. In mathematical terms, this procedure can be represented by the general formula, $$P_j(l) = \sum_{i=1}^{l} E(X_i) \quad (3)$$

where "l" is the total number of observed values for the type of information with a known distribution of finite expectation $E(X_i)$ and where $P_j$ is the population estimate for each subset "j" of the original data.

In general, the present invention first calculates an initial number of unique entities needed to fill a first value of a type of information with a known distribution of finite expectation, and then successively calculates a probabilistic incremental number of unique entities needed for a previous value of the information with the known distribution to increase to a subsequent value of the information with the known distribution, until the probabilistic number of unique entities needed to increase to a predetermined value of the information with the known distribution is calculated. The numbers of unique entities calculated with the above procedure is summed to determine a total population size.

A simple example that uses non-human populations to illustrate the general approach could involve the determination of the number of distinct automobiles that enter a mythical nation on an average week day. The country's border checkpoints keep records that describe every car that passes. This record includes the make, model, year of manufacture, and color of every vehicle, but does not contain a unique vehicle identifier (e.g. a license plate number). All of this information is recorded every time a vehicle passes a checkpoint. Since some vehicles pass a checkpoint many times a day, information describing these vehicles will appear in the data set many times.

For security reasons, the Czar of this mythical nation demands to know how many different motor vehicles enter his nation every day. The present invention can answer this question without additional data collection by applying the procedure described above to the routine administrative database created by the border checkpoints.

For purposes of this example, we will assume that all automobiles on our mythical county's continent are manufactured by one of ten automobile companies, and that the continent's vehicles include each of these makes in equal numbers.

The first operation in the process would be to summarize the contents of the database for a single day. In our example we will say that automobiles passed entry check points in our country 100 times on the 26th of July, and that six of the ten automobile manufacturers were represented in the data base for that day. The facts that six makes of automobile were observed and that each make is equally represented in the total pool of automobiles are the only information required by the present invention to determine the number of unique automobiles represented in the data set for July 26.

In order to determine the total number of unique automobiles represented, the problem is broken down into six distinct problems. The first problem is to determine the number of automobiles that would need to pass a checkpoint before two makes were represented (probability theory says 1.11 automobiles would meet this requirement). The second problem is to determine the number of additional automobiles that would need to pass before three automobiles makes would be observed (probability theory says 1.25 additional automobiles would meet this requirement).

TABLE 1

Results of probabilistic calculations for simple example, assuming ten makes of automobiles with equal representation in the total pool of vehicles.

| | Observed[1] | | | | | | | | |
|---|---|---|---|---|---|---|---|---|---|
| | 1 | 2 | 3 | 4 | 5 | 6 | 7 | 8 | 9 |
| Increment[2] | 1.11 | 1.25 | 1.43 | 1.67 | 2.00 | 2.50 | 3.33 | 5.00 | 10.00 |
| Total[3] | 1.11 | 2.36 | 3.79 | 5.46 | 7.46 | 9.96 | 13.29 | 18.29 | 29.29 |

[1]Number of observed automobile makes.
[2]Number of unique automobiles to increase the number of observed makes from the previous but not to exceed the subsequent number of makes.
[3]Number of unique automobiles to produce the observed number of automobile makes.

Continuing, as illustrated in Table 1 above, through the problem of determining the number of additional automobiles that would need to pass after five automobile makes were observed but before seven automobile makes would be observed (probability theory says 2.5 additional automobiles would meet this requirement). The answer to the Czar's problem is the sum of the answers to these six problems (9.96=1.11+1.25+1.43+1.67+2.0+2.5 automobiles).

When all makes of automobile are observed (probability theory says this will occur when 28.29 automobiles are represented in the data set) it is necessary to introduce another characteristic of the automobiles into the calculations (the color or the year of manufacture, for instance). This procedure will be discussed in more detail below.

In a preferred embodiment of the present invention, the number of observed birth dates "l" is calculated for each gender/year of birth cohort "j" and these parts are considered independently. The number of people necessary to produce a single date of birth is calculated, the number of people necessary to produce a second date of birth after a first has already been observed is calculated, and so forth until the number of birth dates observed in the cohort is achieved.

In other words, a preferred embodiment of the present invention first calculates a probabilistic number of individuals needed to fill one birth date and then successively calculates a probabilistic incremental number of individuals needed for a previous number of dates of birth to increase to a subsequent number of dates of birth, until the probabilistic number of individuals needed to increase to the total number of unique dates of birth is calculated. The results of these calculations are then summed to provide the determination of the original problem (i.e., the number of people necessary to produce the total observed birth dates for a particular gender/year of birth cohort). For birth dates, where a uniform distribution is appropriate, the number of individuals is determined by $$P_j(l) = \sum_{i=1}^{l} \frac{365}{365-i} \quad (4)$$

and the variance of the number of people is determined by $$\sigma^2(P_j(l)) = \sum_{i=1}^{l} \frac{(i \times 365)}{(365-i)^2} \quad (5)$$

Thus, a preferred embodiment of the present invention answers the question "How many people would need to be represented in a data set to produce a specific number of observed combinations of birth date (month, day, and year) and gender?" Probabilistically, the odds that at least two people in a randomly assembled group of 23 people will share a month and day of birth are 50—50. If a room of randomly assembled individuals had 23 different birth dates, the size of the group could be probabilistically estimated to be 24.6 (plus or minus 0.9). Applied to large data set having gender and birth data, similar mathematical reasoning makes it possible to predict the number of individuals represented in a database.

A preferred embodiment of the present invention also determines overlap between two data sets that do not include a unique individual identifier. To find the population overlap, the present invention employs the same decomposition approach that is used to determine population size. First, the present invention applies the procedure described above for determining the population size of the first and second original data sets. Then, the probabilistic number of individuals needed for a larger total number of unique birth dates from either of the first and second data sets to increase to a total number of unique birth dates in the combined data set is calculated. This calculation is similar to the approach used in determining population size and can be represented by the general formula $$P_j(b, c) = \sum_{k=b+1}^{c} E(X_k) \quad (6)$$

where $P_j(b,c)$ is the population estimate for a gender/year of birth cohort "j" necessary for the larger total number of unique birth dates from either of the first and second data sets ("b") to increase to a total number of unique birth dates in the combined data set ("c"), and where $E(X_k)$ is the finite expectation of the variable being measured.

The actual population overlap is the difference between a smaller of the population size of the first and second data sets and the probabilistic number of individuals needed for the larger total number of unique birth dates from either of the first and second data sets to increase to the total number of unique birth dates in the combined data set.

In the simple example introduced above, once the Czar learns the number of distinct automobiles entering his country, the Czar demands to know how many of these automobiles had been issued parking tickets in his country on the same day they entered the country. Although the parking ticket database includes a unique automobile identifier, it does not specify whether the vehicle entered the country on the day the parking ticket was issued. The present invention can answer the Czar's question by determining the overlap between the border checkpoint data set and the parking ticket data set for any specified day.

The first operation is to summarize the contents of the parking ticket data base and a combined (concatenated) parking ticket and border check point data base for the 26th of July in the same way that the border check point data base was summarized earlier. In our example, we will say that nine parking tickets were issued to eight unique automobiles that represented five automobile manufacturers. The combined database includes 109 records that describe automobiles that represent seven manufacturers.

A two-operation process is used to determine the total number of unique automobiles that received parking tickets on the day they entered the country. First, the number of unique automobiles required to increase the number of observed automobile makes from the number of automobile makes in the larger of the two original data sets to the number of automobile makes observed in the combined data set is calculated. In this example, probability theory says that 3.33 unique automobiles are required to increase from the six makes in the checkpoint database to the seven makes in the combined data set (Table 1). Second, the result of the above calculation is subtracted from the number of automobiles in the smaller of the two original data sets to determine the number of unique automobiles that received parking tickets on the same day as they entered the country. In this simple example, the answer to the Czar's question is 4.67 automobiles. This result is obtained by subtracting 3.33 (the number of unique automobiles that are required to increase from the six makes in the check point data base to the seven makes in the combined data base) from eight (the number of automobiles in the parking ticket data base according to its true unique automobile identifier).

The present invention is also superior to Larsen's formulation in that a preferred embodiment of the present invention may utilize any known distribution (e.g. uniform, lognormal, negative exponential, etc) of personal characteristics. In the prior art, only the uniform distribution could be used. In a preferred embodiment of the present invention, a uniform distribution with 365 (or 366) categories to model date of birth is used, but the present invention can be applied to any known distribution with finite expectation.

Reference will now be made in detail to further preferred embodiments of the present invention, examples of which are illustrated in the accompanying drawings, wherein like reference numerals refer to like elements throughout. The following preferred embodiment, using data on birth and gender, is merely exemplary of the present invention. However, the present invention is more widely applicable, as illustrated in the simple automobile example and as discussed below.

FIG. 1 shows a preferred embodiment of a population size and overlap determination apparatus 100 according to the present invention. The apparatus 100 measures the number of people represented in a data set that does not contain a unique personal identifier, but does contain information on enduring personal characteristics for which the distribution in the general population is known. The apparatus 100 also measures the number of people who are represented in more than one data set when no common unique identifiers are shared across data sets.

The apparatus 100 includes a storage medium 10 and a computer 20. The computer 20 may be a general purpose computer, or the like, that can execute software programs and instructions. The computer 20 includes a data preparation process or unit 22, a population size measurement process or unit 24, a population overlap measurement process or unit 26, and a total population information generator 28.

The storage medium 10 may be an electronic storage medium, including magneto-optical disks, RAM, ROM, CDs, diskettes, or the like, that can store a data set 1, a data set 2, a combined data set 3, and an aggregate data set 4 used by the apparatus 100, as well as the processes described herein. Each data set may also be stored in separate storage mediums. An output file 5 contains the output generated by the apparatus 100. While the output file 5 is depicted in FIG. 1, the output may also be a data set, a printed report, a display on a computer screen, or any other medium for presenting the analysis and results generated by the present invention.

Figure 2:
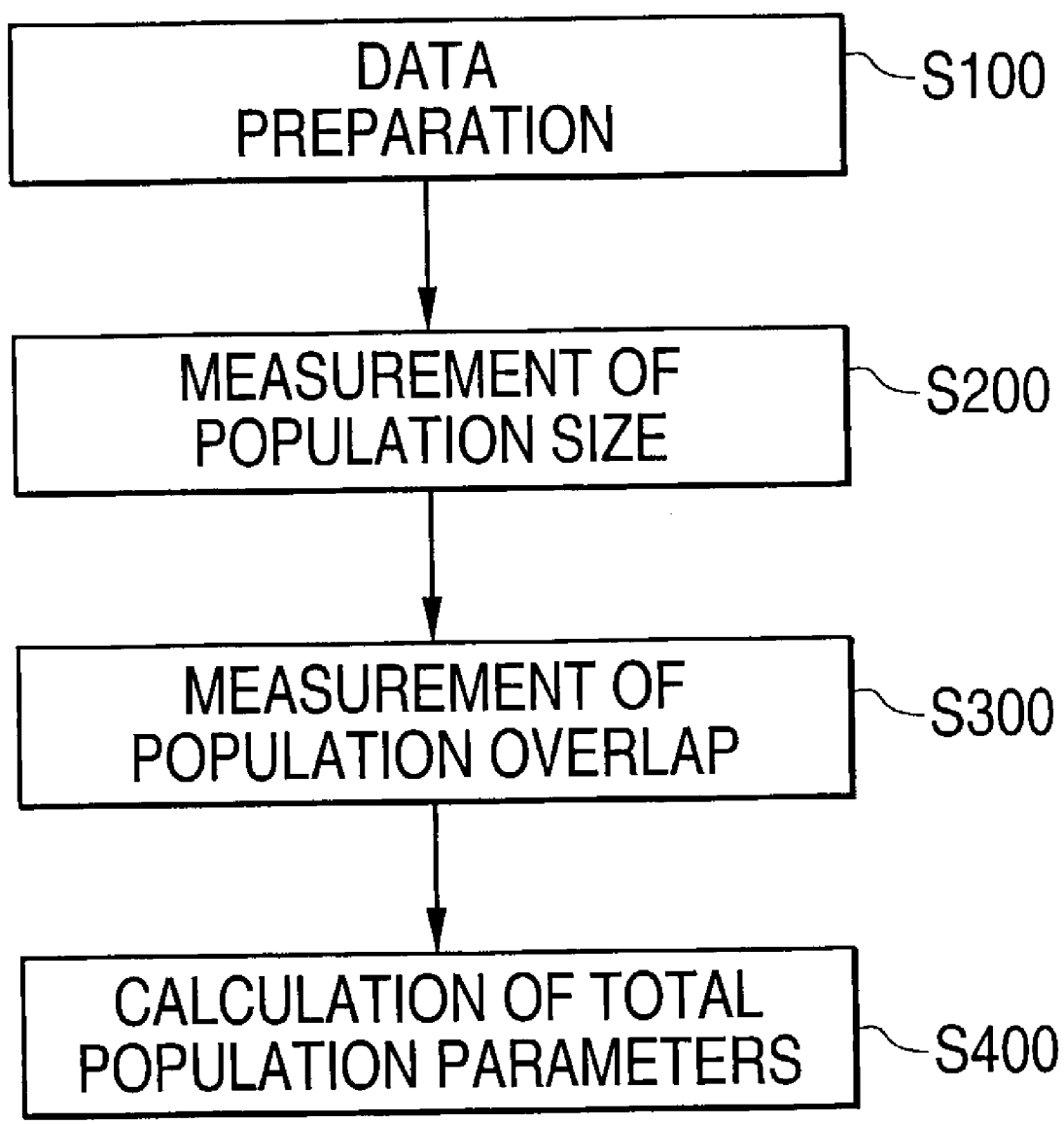
FIG. 2 is a flow chart describing operations performed by corresponding processing units in a computer 20 of FIG. 1.

FIG. 2 depicts operations performed by corresponding units in the computer 20. The data preparation unit 22 executes a data preparation operation S100, the population size measurement unit 24 executes a measurement of population size operation S200, the population overlap measurement unit 26 executes a measurement of population overlap operation S300, and the total population information generator 28 executes a calculation of total population parameters operation S400.

Figure 3:
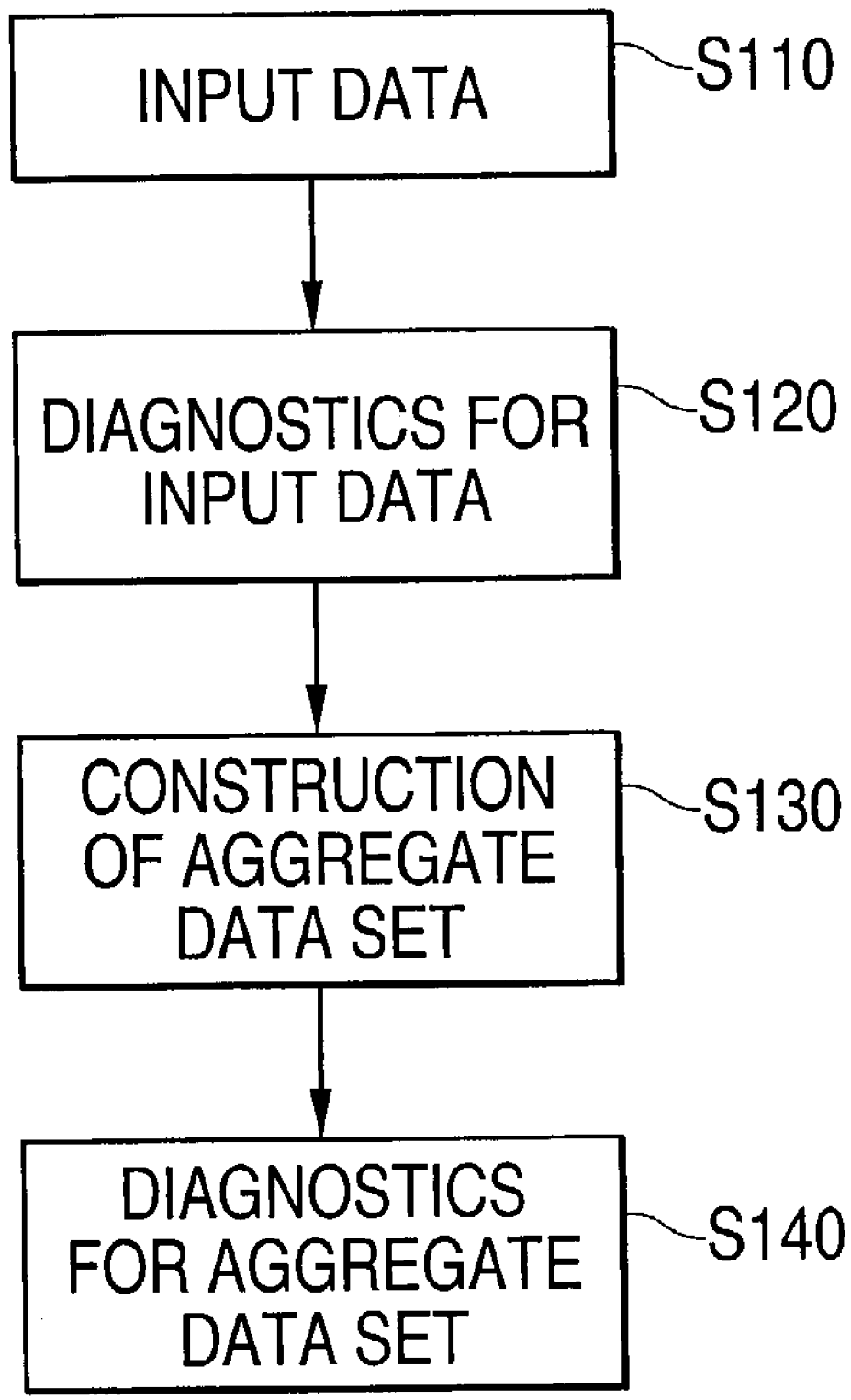
FIG. 3 is a flow chart describing operations corresponding to a data preparation operation S100 of FIG. 2.

FIG. 3 is a flowchart depicting operations performed by the data preparation unit 22 in the data preparation operation S100. In an input data operation S110, the computer 20 receives input data stored in data sets 1 and 2. The input data consists of discrete records that describe individuals, events, or objects that relate to individuals. The data sets 1 and 2 may contain one record per person or multiple records per person. In the present preferred embodiment, each record contains the date of birth (year, month, and day) of the person it pertains to. Information on the gender of the person is also utilized in the preferred embodiment described here. However, other attributes of people that have known probability distributions in the general population may be used in place of the date of birth. For instance, other information pertinent to specific analytical interests (including, but not limited to, clinical, economic, and social-demographic characteristics of the person) may be included as well. The data sets 1 and 2 may also be defined by, for example, organizational, geographical, temporal, fiscal, or other characteristics.

In a diagnostics for input data operation S120, the distribution of month of birth and day of birth in each data set 1 and 2 is compared to theoretical distributions of day of the month, and month of the year (i.e., thirty to thirty-one days per month and twelve months per year). When a different variable with a known distribution is used (e.g. HLA blood type, eye color, etc.), the observed distribution is compared to the expected distribution. The results of all diagnostics, including the nature and amount of any discrepancies between observed and theoretical distributions, will be included in the output file 5. When there are gross discrepancies between the observed and the expected distributions, a warning will be generated (e.g., included in the output file 5). This warning will indicate that the assumptions underlying the preferred embodiment may not hold. Possible alternatives include consulting with the organization that produced the data set, and consideration of alternative partitioning of the data set.

In a construction of aggregate data set operation S130, the combined data set 3 is constructed (concatenated) from each of the original data sets 1 and 2 and the data from each of these three data sets (the data set 1, the data set 2, and the combined data set 3) are aggregated to create a fourth data set, i.e. an aggregate data set 4. In this preferred embodiment, each record in the aggregate data set 4 pertains to a gender and year of birth combination (e.g. men born in 1945, women born in 1945, men born in 1946, etc.). In addition, each record in the aggregate data set 4 includes seven types of information. These types of information include specifications for the year of birth and gender the record describes, and the number of birth dates for that year of birth and gender that appeared in each of the three data sets (the data set 1, the data set 2, and the combined data set 3), and the number of unique individuals represented in the two original data sets 1 and 2 when this is known.

The construction of aggregate data set operation S130, and the other operations that follow, may be performed for any subcategory of analytical interest for which data is available in one or both of the original data sets 1 and 2 (e.g. people from a specified geographical area, people with a specified disorder, and people in a specified demographic category) when subcategory specific size and overlap parameters are desired.

In a diagnostics for combined data set operation S140, the number of dates of birth represented in each record of the aggregate data set 4 is compared to the maximum possible (e.g. the total number of days in the year) and the frequency distribution is reported in the output file 5. If the number of days represented is equal to the maximum possible, a fatal error warning is issued, and possible solutions to the problem are included in the output file 5. The possible solutions to the problem are listed below in order of preference.

1. Another enduring personal attribute is added and the construction of aggregate data set operation S130 is repeated. If ethnicity were added, for instance, each record in the aggregate data set 4 would pertain to a specific gender, year of birth, and ethnicity combination (e.g., white men born in 1945, non-white men born in 1945, white women born in 1945, non-white women born in 1945, white men born in 1946, etc.). Each record would include specifications for the year of birth, gender and ethnicity it describes, and the number of birth dates for that year of birth, gender, and ethnicity that appeared in the input data sets 1, 2, and 3.

2. The scope of the aggregate records can be expanded so that the number of observed birth dates is less than the largest possible number. This can be accomplished by joining a year in which the number of dates of births is less than the possible number, to a year for which the number of possible dates of birth is equal to the maximum possible. For example, if 365 birth dates were observed for men born in 1945 and 345 birth dates were observed for men born in 1946, combining the two years would result in a time period for which 710 of a possible 730 birth dates was observed. In this case the record in the aggregate data set 4 would be redefined to describe men born in 1945 or 1946. Application of this solution requires that all appropriate elements of the computer programming operations be modified to specify the maximum possible number of days in the redefined record.

3. When necessary, a combination of the two above-described solutions is used to solve the problem.

When the number of days represented in one of the records in the aggregate data set 4 approaches the maximum possible, a warning is added to the output file 5. The warning will include a description of the first two options listed above.

Figure 4:
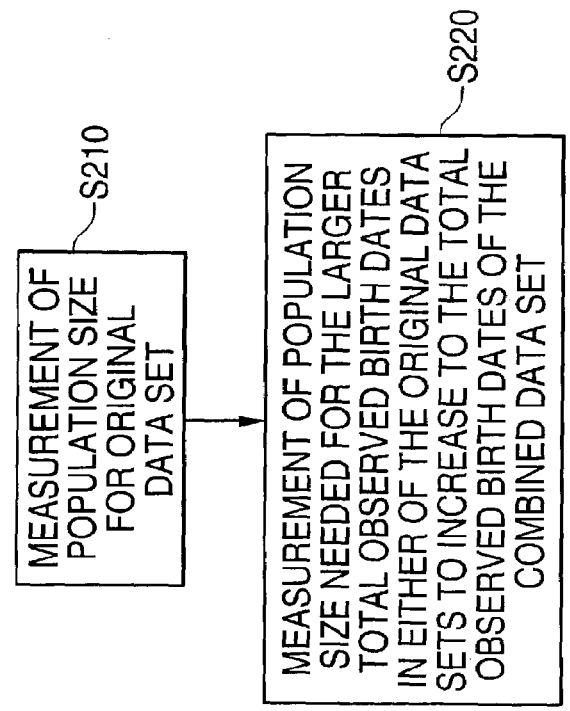
FIG. 4 is a flow chart describing operations corresponding to a measurement of population size operation S200 of FIG. 2.

FIG. 4 is a flow chart describing operations corresponding to the measurement of population size operation S200. The probabilistic determination of population size in the measurement of population size operation S200 is conducted for each record in the aggregate data set 4. A population size is determined for each of the original data sets 1 and 2 in operation S210. In addition, the population size necessary for the number of observed birth dates from the data set 1 or 2 having the larger number of observed birth dates to increase to the number of birth dates observed in the combined data set 3 is determined in operation S220.

In a measurement of population size for original data set operation S210, for each gender/year of birth cohort record "j" in the aggregate data set 4 with "I" number of birthdays in either the data set 1 or 2, the number of people represented in the subset is determined by equation 7:

$$P_j(l) = \sum_{i=1}^{l} \frac{365}{365 - i} \quad (7)$$

Figure 6:
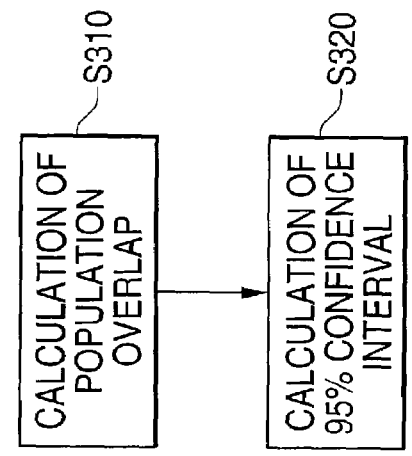
FIG. 6 is a flow chart describing operations corresponding to a measurement of population overlap operation S300 of FIG. 2.

Equation 7 determines the population size of each data set 1 and 2 for each gender/year of birth cohort by calculating the probabilistic number of individuals needed to fill one birth date, plus the probabilistic incremental number of individuals needed to increase from one birth date and fill a second birth date, plus the probabilistic incremental number of individuals needed to fill a third birth date, and so on, until the probabilistic number of individuals needed to fill the total observed birth dates is calculated. As depicted in FIG. 6, the number of individuals needed to fill a first date of birth is calculated in operation S211. Then, in operation S212, this preferred embodiment of the present invention successively calculates a probabilistic incremental number of individuals needed for a previous number of dates of birth to increase to a subsequent number of dates of birth, until the probabilistic number of unique entities needed to increase to the total predetermined number of unique dates of birth is calculated (operation S213 checks if the predetermined number of dates of birth have been filled). In operation S214, the number of individuals calculated above is summed to provide the population size of data sets 1 and 2 for each gender/year of birth cohort, "j". The resulting values become part of each record in the aggregate data set 4. When the year is a leap year, the value 365 is replaced by 366 in equation 1 and all subsequent equations.

For each record in the aggregate data set 4 with "I" number of birthdays, the variance of the number of people represented in the subset is determined by equation 8:

$$\sigma^2(P_j(l)) = \sum_{i=1}^{l} \frac{(i \times 365)}{(365 - i)^2} \quad (8)$$

In operation S220, a determination is made as to the population size necessary for the number of birth dates from the number observed in the larger of the two original data sets 1 and 2 to increase to the number of birth dates observed in the combined data set 3. When the number of birth dates in the larger original data set is smaller than the number in the combined data set, the measurement of operation S220 is determined by equation 9:

$$P_j(b, c) = \sum_{k=b+1}^{c} \frac{365}{365 - k} \quad (9)$$

where $P_j(b,c)$ is the population estimate for a gender/year of birth cohort "j" necessary for the larger total number of unique birth dates from either of the first and second data sets ("b") to increase to a total number of unique birth dates in the combined data set ("c").

For each record in the aggregate data set 4, the variance $\sigma^2(P_j(b,c))$ of the number of people necessary to increase the number of observed birth dates from the number of birth dates observed in the larger of the two original data sets 1 and 2 to the number of birth dates observed in the combined data set 3 is determined by equation 10:

$$\sigma^2(P_j(b, c)) = \sum_{k=b+1}^{c} \frac{(k \times 365)}{(365 - k)^2} \quad (10)$$

As a result of the above calculations, six new data elements are added to each record in the aggregate data set 4. The first two data elements are the determined population size for each of the two original data sets 1 and 2. The second two data elements are the variance of this population size for each of the two original data sets 1 and 2. The last two variables are the number of people necessary for the number of birth dates to increase from the number observed in the larger of the two of the original data sets 1 and 2 to the number observed in the combined data set 3, and the variance for this value.

FIG. 6 is a flow chart describing operations corresponding to the measurement of population overlap operation S300. In a calculation of population overlap operation S310, probabilistic determination of population overlap is conducted for each record in the aggregate data set 4. Population overlap is the difference between the number of people represented in the smaller of the two original data sets 1 and 2 and the number of people needed for the increase in the number of birth dates observed from the larger of the two original data sets 1 and 2 to the combined data set 3. Calculating population overlap depends on whether the smaller number of individuals represented in either the original data sets 1 or 2 is known (based on a data set specific unique person identifier) or has been statistically determined by the operations identified above.

The calculation of population overlap operation S310 is determined by equation 11:

$$P(\text{overlap}) = P(a) - P(b,c) \quad (11)$$

where P(a) is the number of people represented (population size) in the smaller data set and P(b,c) is the population size necessary for increasing the number of birth dates observed in the larger (i.e., having more observed birth dates) of the two original data sets 1 and 2 to the number of birth dates observed in the combined data set 3. P(a) is the actual number of people when this number is known. When this number is not known, P(a) is the number determined by the calculations above.

When the sum of the number of birth dates in the two original data sets 1 and 2 is equal to the number of birth dates in the combined data set 3, the overlap is set to zero. When the population overlap derived by the above operation S310 is less than zero, the population overlap parameter is set to zero, which is the smallest overlap possible.

Calculating the variance of the population overlap $\sigma_P^2$ (overlap) is determined by equation 12:

$$\sigma_P^2(\text{overlap}) = \sigma^2(P(a)) + \sigma^2(P(b,c)) \quad (12)$$

where $\sigma^2(P(a))$ is the variance of the number of people represented (population size) in the smaller data set and $\sigma^2(P(b,c))$ is variance of the population size necessary for increasing the number of birth dates observed in the larger (i.e., having more observed birth dates) of the two original data sets 1 and 2 to the number of birth dates observed in the combined data set 3. The variance of the population size in the smaller data set $\sigma^2(P(a))$ is equal to zero when the number of people is known, and is calculated using equation (8) when the number of people is not known. When the sum of the number of birth dates in the two original data sets 1 and 2 is equal to the number of birth dates in the combined data set 3, the variance of the overlap $\sigma_P^2$ (overlap) is set to zero.

In a calculation of 95% confidence interval operation S320, 95% confidence intervals are calculated as the determination of population overlap, plus and minus 1.96 times the standard deviation (square root of variance) determined in equation (12). In some cases, this calculation operation S320 will result in a range that includes impossible values (i.e. negative values, or values greater than the known number of individuals). In order to eliminate variance that is impossible, separate variance parameters are calculated for the low side and the high side of the overlap parameter. This results in an asymmetric confidence interval. These considerations will be invoked under the following conditions.

1. When the variance around the overlap parameter includes a negative number, the variance for the low side of the parameter is decreased so that the overlap parameter minus 1.96 times the standard deviation is zero. For example, when the calculations indicate that a record includes an overlap of 3 people and the variance is 4 people, these parameters include the theoretical possibility of −1 person, a practical impossibility. In this case the variance parameter for the low side of the population parameter would be decreased to 2.25.

2. When the variance around the overlap parameter includes a number that is greater than the known number of people in the smaller of the two original data sets, the variance for the high side of the parameter is decreased so that the overlap parameter plus 1.96 times the standard deviation is equal to the number of people in the smaller of the two data sets. This will only be detectable when the smaller of the data sets 1 and 2 include a data set specific unique person identifier.

Three new variables are added to each record of the aggregate data set 4 as a result of operation S320. These include the determination of population overlap, and the two components (low side and high side) of the asymmetrical variance associated with the overlap.

Figure 7:
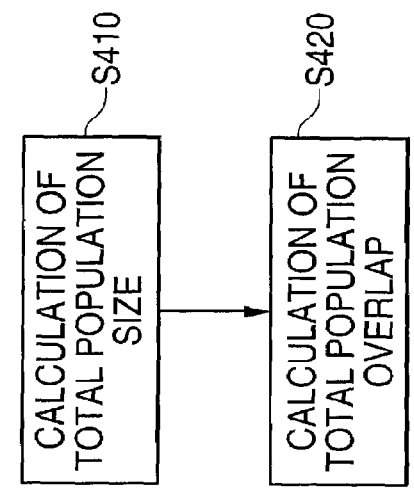
FIG. 7 is a flow chart describing operations corresponding to a calculation of total population parameters operation S400 of FIG. 2.

FIG. 7 is a flow chart describing operations corresponding to the calculation of total population parameters operation S400. As mentioned above, the results of the probabilistic measurement of population size operation S200 and the measurement of population overlap operation S300 includes the population size and overlap parameters for the input data sets 1 and 2. Population size parameters include the determination of the number of people represented in each of the original data sets 1 and 2, and verification of these parameters for data sets that included unique person identifiers. Population overlap parameters include the number of people represented in both data sets (with 95% confidence intervals).

In a calculation of total population size operation S410, parameters for the total number of people represented in the two original data sets 1 and 2 and the confidence limits for this parameter are obtained by combining the results for every record in the aggregate data set 4. The total number of people $P_{Total}$ is obtained by summing the population parameters over all "k" records (or gender/year of birth cohort subsets) as in equation 13:

$$P_{Total} = \sum^{k} P_j \quad (13)$$

and the total variance $\sigma^2(\text{Total})$ is obtained by summing the variance for each record as in equation 14:

$$\sigma^2(\text{Total}) = \sum_{j=1}^{k} \sigma^2(P_J) \quad (14)$$

where k is the total number of records in the aggregate data set 4. The estimate of the 95% confidence interval is constructed as in equation 15:

$$P_j \pm 1.96 \sigma(P_j) \quad (15)$$

When an original data set contained a unique person identifier, the statistically derived population parameter is compared to the parameter indicated by the unique identifier in the original data set. This comparison provides a data set specific verification of the statistical procedure. The results of this verification procedure are reported in the output file 5 in all cases. When the actual number of people is not included within the confidence interval of the determined parameter, a warning is issued in the output file 5. If the probabilistic population parameter does not include the actual number of people, this result may indicate that the original data set did not conform to assumptions about the equal probability of birth dates, may indicate that the unique identifier provided with the original data is flawed, or the result may be the predictable one in twenty cases in which the 95% confidence interval does not contain the true value.

In a calculation of total population overlap operation S420, parameters for the number of people represented in both of the original data sets 1 and 2 and the confidence limits for this parameter are obtained by combining the results for every record in the aggregate data set 4. The total number of people overlapping $P_{Total\ Overlap}$ is obtained by summing the overlap parameters $P_j(\text{overlap})$ over all "k" records as in equation 16:

$$P_{Total\ Overlap} = \sum_{j=1}^{k} P_j(\text{overlap}) \qquad (16)$$

The lower variance is obtained by summing the lower variance for the overlap parameter from each record, and the upper variance is obtained by summing the upper variance for the overlap parameter from each record. Equation 17:

$$\sigma^2(LowerTotal) = \sum_{j=1}^{k} \sigma^2(Lower\ P_j) \qquad (17)$$

presents the computation for the lower variance $\sigma^2$(Lower Total) where k is a counter for the number of records in the complete data set. A similar equation provides the upper variance of the overlap parameter for the complete data set.

The estimate of the 95% confidence interval is constructed as in equation 18:

$$P-1.96\sigma(\text{lower}),\ P+1.96\sigma(\text{upper}) \qquad (18)$$

Additional output to the output file 5 may include size and overlap parameters for age and gender categories, or for other categories of people for which basic information is available in one or both of the original data sets 1 and 2. Age and gender reporting may be provided by additional levels of summation at the output stage of the process. The determination of parameters for other pertinent characteristics may be obtained by repeating the entire analytical process for each desired reporting category, or by expanding the record to include parameters for the desired person characteristics.

According to a population size and overlap determination apparatus and method according to a preferred embodiment of the present invention, a more accurate and superior population size and overlap determination between multiple data sources may be made. As mentioned above, the present invention builds upon the classical occupancy theory, but utilizes a fundamentally different, and far superior, operationalization of the classical occupancy theory than conventional techniques. In fundamental contrast to Larsen, the present invention solves the classical occupancy problem using random variable decomposition techniques, without resort to approximation. The present invention is able to provide a determination of population size and variance that is based on a different probabilistic method.

The present invention is superior to the approach proposed by Larsen in three ways. First, the present invention is superior because it is more flexible. It can determine population size even when the known characteristics of members are not uniformly distributed. For example, if a data set included information on HLA blood type, which has a known, but non-uniform distribution, the number of individuals represented in the data set can be determined by the present invention. Second, the present invention always provides smaller coefficients of variation than Larsen's. FIG. 8 shows that calculation of the coefficient of variation for each of the two approaches indicates that the present invention will always produce smaller coefficients of variation than Larsen's maximum likelihood solution to his approximation of the classical occupancy problem. Third, the present invention allows for the direct determination of population overlap. In order to estimate the number of individuals who are represented in both of two distinct data sets, neither of which includes a true unique individual identifier, the procedure described above can simply be applied three times; once each to the separate data sets, and once to a combined data set. While the difference between the sum of the estimates for the two distinct data sets and the estimate for the combined data set is an estimate of the number of individuals who are represented in both data sets, such a procedure, however, would result in an exaggerated error statement. Thus, in order to provide a more reasonable confidence interval, the present invention estimates the number of unique individuals that are added when the smaller number of observed birth dates of either the first or second data set is added to the number of observed birth dates of the larger combined data set.

While a preferred embodiment was described above, the present invention is not limited to the population size and overlap determination apparatus of the above embodiment. For example, the data preparation unit 22, the population size measurement unit 24, the population overlap measurement unit 26, and the total population information generator 28 may be segments of a computer program embodied on a computer-readable medium. Also, more than two original input data sets may be provided. It is to be understood that the present invention is generally applicable to determining the parameters of overlap associated with multiple data sets.

In addition, other personal characteristics may, of course, be used. The above embodiment performed analysis based on date of birth and gender. However, the present invention may also use any enduring personal characteristic or non-changeable phenomena for which the distribution in the general population is known and finite. Moreover, the above embodiment focused on human populations. It is to be understood, however, that the present invention is also applicable to nonhuman populations (including animate and inanimate objects) for which one or more characteristics of individual elements/members are variable and have a known distribution in the larger class of objects.

While the above-described preferred embodiments addressed the situation where there are no unique identifiers for unique entities in first and second data sets, the present invention is also applicable to the probabilistic determination of population overlap when there are unique identifiers for unique entities in the first and second data sets, but the type of unique identifiers in the first data set are different from the type of unique identifiers used in the second data set. For instance, people's social security numbers may be used in a first data set, while unique proprietary insurance policy numbers are used instead in a second data set. Therefore, the population size may be accurately determined using the respective (but different) unique identifiers for the first and second data sets. However, since the unique identifiers are not of the same type (e.g., no correlation between social security numbers in the first data set and the proprietary insurance policy numbers in the second data set, in this example), the problem of overlap determination still exists. In this example, the population overlap may still be determined with the probabilistic population overlap determination of the preferred embodiments described above.

As described above, the method and apparatus requires access to records that include date of birth include private data (See Statistics in Medicine previously cited). The method and apparatus as described above uses records that included individuals' complete dates of birth. This information is used to construct an aggregate data set (data set 4 created at operation S130) that contains seven types of information that can be called data subset information and distribution occurrence information. These types of information include the year of birth and gender the record describes, and the number of birth dates for that year of birth and gender that appeared in each of the three data sets (the data set 1, the data set 2, and the combined data set 3), and the number of unique individuals represented in the two original data sets 1 and 2 when this is known. The data sets 1 and 2 could also include other types of identifying information, such as social security number, fingerprint, home address, telephone number, facial picture, etc., that would not be included in data set 4. As a result, the records included in this data set (data set 4) meet or exceed emerging privacy standards because they do not include any dates of birth. The present invention as described below allows the records of data set 4 to be created by the data holder, such as a government health service, and the holder forwards the data set 4 records to a processor. The processor determines the size and overlap and returns the information to the data holder. In this way, the privacy of the information contained in the original and created data sets is further protected.

The system of the present invention allowing the enhanced privacy preferably has a system configuration 400 as depicted in FIG. 9 where a computer 410 is used by a estimate processor or vendor (not shown) via a display 412 to transfer a diagnostic procedure 414 and an aggregate procedure 416 (see Appendix I) in a database 418 over a communication facility 420, such as the internet network, to a computer 422 of a data holder or customer (not shown), such as an employee of a state agency. The computer 422 is used by the data holder to apply the diagnostic procedure 414 to data sets 1 and 2 (see also FIG. 1) in database 426 to diagnose problems in the data sets. The problems discovered can be corrected and the diagnostic procedure 414 executed again. Once the input data is suitable, the aggregate procedure 416 is applied to the data sets 1 and 2 creating the combined data set 3 and the aggregate data set 4. The aggregate data set 4 is transferred over the network 420 to computer 410 where it is stored in the database 418. The estimate procedure or PPE 428, as previously described herein, is applied to the aggregate data set 4 in the database 418 to produce the caseload site B 430 and overlap 432 data. This data is then sent to the data holder computer 422 where it is displayed on display 424.

As can be surmised from the above discussion, the enhance privacy method includes five operations (see FIG. 10). In the first operation S510 the vendor transfers the computer programs or procedures to the customer accompanied by the diagnostic instructions as set forth in the Appendix I. This can be accomplished by sending the programs as email file attachments over a network as discussed previously. The files can also be transferred by a direct connection between the computers 410 and 422. The procedures can also be stored on a medium, such as a floppy disc, and sent to the customer by mail or other physical conveyance. That is the procedures can be provided to the customer in any convenient way.

These procedures and instructions of Appendix I are for data sets containing information about humans. One of ordinary skill in the art can adapt these procedures and instructions for other types of data sets such as automobiles crossing a national border.

The customer applies the computer programs to the person level data set. This is done by making a change in each of the programs of the Appendix I to identify the path to the data sets, such as by entering the complete file names.

The diagnostics procedure evaluates customer data sets with regard to suitability for PPE (or other procedures for determining caseload size and overlap). Suitability is evaluated with reference to completeness of information on date of birth, gender, and other relevant information; the distribution of birthdays within a month and birth months within a year; and the number of dates of birth evident for each year of birth/gender combination. The customer uses the diagnostic procedure to evaluate each data set. That is, the procedure determines the quality of the data.

The diagnostic program also evaluates the data sets in terms of valid codes or values, distributions of days and months of birth, the number of dates of birth in each birth cohort, and provides a summary of the results of these procedures. Four fields are evaluated for valid codes: day of birth, month of birth, year of birth, and gender. Each is assessed for missing values and for invalid values. The number and proportion of records with invalid values and with missing values are reported. A warning is issued if the percentage of valid records falls below 75%.

The diagnostic program also evaluates the data sets with regard to the distribution of dates of birth within months and the distribution of months within years. The distributions of days within months is compared to an expected percent. The expected value for days between 1 and 28 are the same but differ from the values for 29–31. The distributions of months within the year are compared to an expected percent that is based on vital records statistics. The ratio between the observed and the expected number of observations is calculated and graphed. If this ratio is greater than 2 or less than 25, a warning is issued.

At the end, the diagnostic program summarizes for the customer the findings of these diagnostic operations. If desired, records with errors are removed from the data sets or they can be fixed by the customer. An example of the output of the diagnostic procedure for analyzing data sets of humans with dates of birth is set forth in the Appendix II. A similar output can be created for other types of information by one of ordinary skill in the art.

If all of the data sets are found to be suitable for further analysis, the second computer program, the aggregate procedure, is applied to the data sets. If any of the data sets are found to be unsuitable, possible remedial steps can be provided and the diagnostic program will be applied again.

The aggregate procedure counts the number of days of birth that occur in each year-of-birth/gender cohort represented in the data set. If 365 days of birth (or 366 in a leap year) are observed, a fatal warning is issued stating that approach of the invention cannot be run on the existing data set. When the number of days of birth is less than 365 but greater than 355, a warning is issued, stating that the observed number of days of birth is approaching the maximum value.

The aggregate procedure also combines the two data sets 1 and 2 to create the combined data set 3 and stores it in the database. The aggregate procedure determines whether the combined data set is too large. The procedure then also essentially counts the number of occurrences with respect the distribution within each data subset and creates the aggregate data records. For human population data sets the aggregate procedure aggregates the component data sets to a year of birth/gender specific record. This record will include the number of dates of birth that are represented in each of the component data sets, the number of dates of birth in all possible combinations of component data sets. The attached computer program of Appendix I provides an example of the procedures when two data sets are involved. The aggregation program evaluates the combined data set in terms of the number of dates of birth in each birth cohort (as described above), provides a summary of the results, and produces an aggregate data file for transport to the vendor.

The customer returns S514 the resulting aggregated data to the vendor. This can be in the form of transferring a file by email, putting the data onto a storage medium, such as a floppy disc and sending the disc by mail, by printing the aggregate data on paper and sending the paper by mail or electronically, by conveying data orally over the telephone or any other way of getting this limited set of data to the vendor. For example, if the data sets included information on programs for children (male and female) of ages 0–18 years, the aggregate data would include 36 lines of data, one for each year and gender, with each line of data including 3 numbers (a number of individuals in data set 1, a number of individuals in data set 2 and a number of individuals in the combined data set). This data can be easily conveyed orally. The data set produced by the computer program executing in the customers computer 422 described above will typically and preferably be electronically transferred to the vendor's computer 410 and stored in the database 418. This data set is the anonymous data set described in operation S130 of the FIG. 3. Note the aggregate data can be created by procedures other than those of the Appendix I.

The vendor analyses S516 the data set transferred by the customer preferably created using the method previously described. However, the analysis can be performed by other procedures to determine caseload size and overlap. The vendor's computer 410 reads the aggregate data, applies operations of the estimation procedure for determining caseload size and overlap, and produces estimates of caseload size and overlap (with 95% confidence intervals). The results are preferably formatted to predetermined report specifications.

Figure 11:
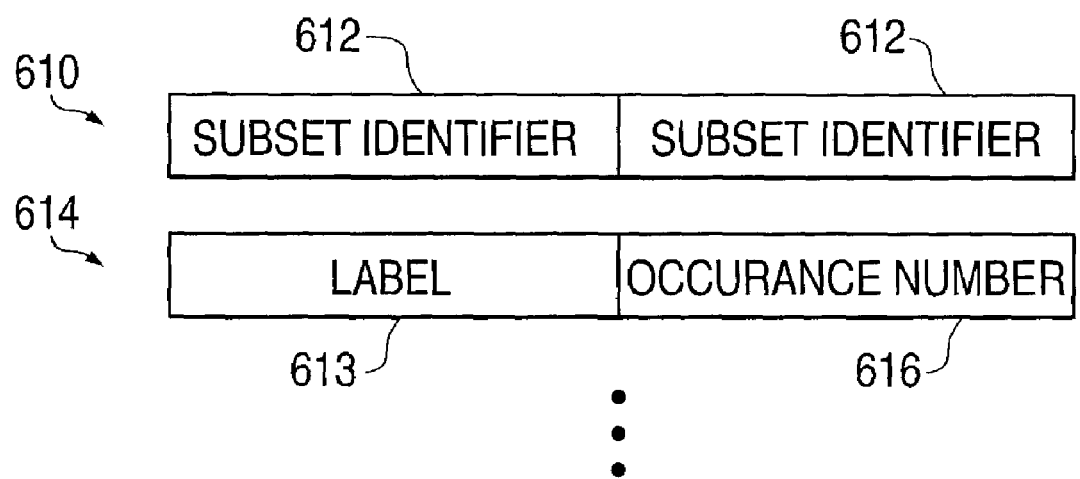
FIG. 11 depicts a data structure of aggregate data transferred during distributed processing

The vendor returns S518 the findings regarding caseload size and overlap to customer. Once again, this can be by transferring a file as an email attachment, placing the file on a transportable storage medium, such as a result floppy disc, printing the results on paper and sending by mail or electronically, by oral telephone call, or any other way of conveniently transferring the results to the customer The aggregate data transferred from the customer to the vendor needs to communicate two types of information. The first type of information is information on how the data of each data set is subdivided or subsetted or is data subset information. For example, for humans it might be gender and date of birth. The second type of information indicates the number of occurrences of a phenomena on the distribution of finite expectation that is used to make the estimate in the decomposition procedure or is distribution occurrence information. In a data structure, such as a list type data structure depicted in FIG. 11, the first record 610 would include subset identifiers fields 612. The subsequent records 614 would include an occurrence number field 615 and an optional label field 618 identifying the subset to which the occurrence count corresponds. Other data structures which provide such information can be used.

Figure 12:
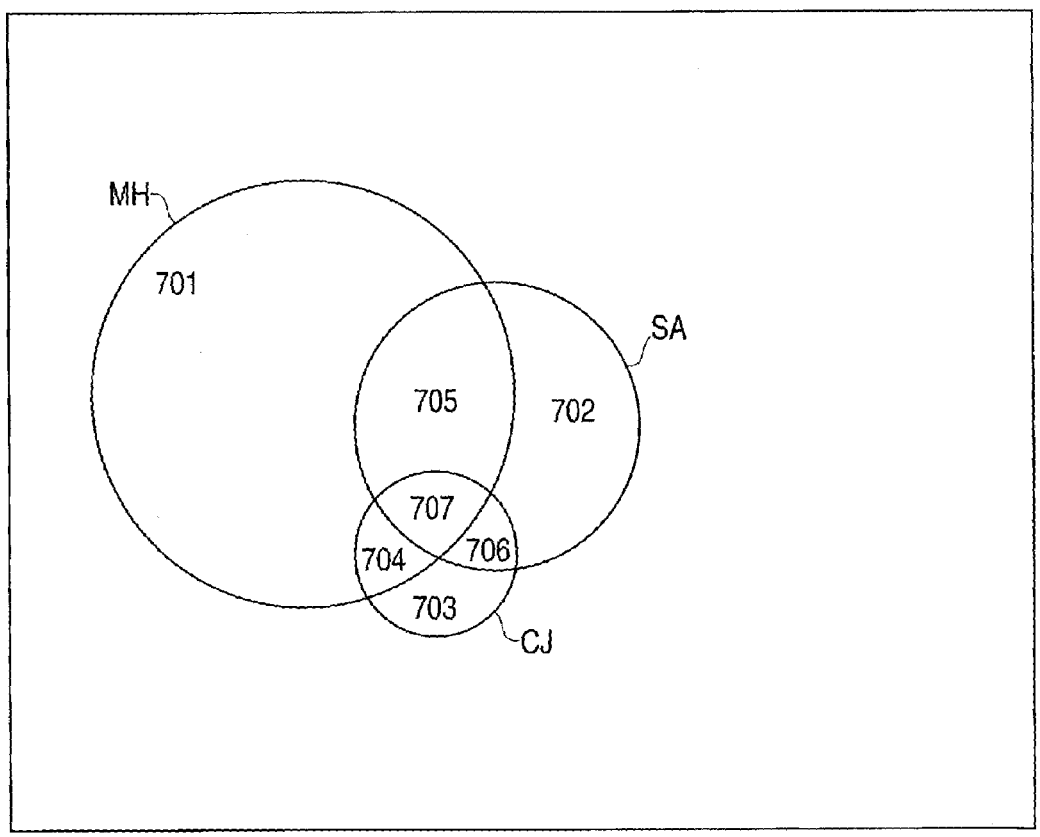
FIG. 12 illustrates a three-way overlap.

As discussed previously there is an interest in determining the size of and overlap of three or more data sets containing records on unique entities without unique identifiers for the unique entities and having at least one common type of information with a known distribution of finite expectation. An example of a three way overlap problem is depicted in FIG. 12 using hypothetical data from three service sectors: mental health (MH), substance abuse (SA), and criminal justice (CJ). The sizes of the data sets are represented by their relative sizes with the MH set being the largest and CJ being the smallest. Each numbered sector (or combination of numbered sectors) provides potentially valuable information on the service sectors involved.

The multiple-way overlap determination approach described herein provides the numbers of people represented in the seven different sub-sectors represented in the diagram, and the combinations of the sectors. Sub-sector 701 represents the individuals who were served by the MH service sector but not by either of the other service sectors. Sub-sector 702 represents the individuals who were served by the SA service sector but not by either of the other service sectors. Similarly, sub-sector 703 represents the individuals who were served by the CJ service sector but not by either of the other service sectors. Sub-sector 704 represents the individuals who were served by both the MH and the CJ service sector but not by the SA sector. Sub-sector 705 represents the individuals who were served by both the MH and the SA service sector but not by the CJ sector. Sub-sector 706 represents the individuals who were served by both the SA and the CJ service sector but not by the MH sector. Sub-sector 707 represents the individuals who were served by all three service sectors (MH, SA, and CJ).

In this example sub-sector 707 is frequently identified as including the individuals most in need of intensive services, service integration, and perhaps addition services. The identification of the number of individuals in sub-sector 707 is frequently the primary objective of a three-way overlap problem. In this example, this is the number of people who were arrested out of the total population of people who received both MH and SA service recipients. This can be expressed as an arrest rate for people who received both MH and SA services by dividing the number of individuals represented in 707 by the sum of the individuals represented in sub-sectors 705 and 707

Sub-sector 706 includes individuals who received SA but not MH services and were arrested. The arrest rate for individuals who only received substance abuse services can be derived by dividing the number of individuals represented in 706 by the sum individuals represented in sub-sectors 702 and 706. This arrest rate is often compared to the arrest rate for individuals who receive MH but not SA services. This rate is derived by dividing sub-sector 704 by the sum of sub-sectors 704 and 701.

Sub-sector 703 includes people who were arrested but did not receive either MH or SA series. These people are frequently identified as individuals in need of services whose need is not being met.

The unduplicated number of individuals receiving MH is derived by adding the numbers of individuals represented in sub-sectors 701, 704, 705, and 707. The unduplicated number of individuals served by the SA and the CJ service sectors can be derived using similar computations.

The present invention can determine estimates for the population size in each of the sectors depicted in FIG. 12 as well as determine the overlap of sector(s) with other sector(s).

Figure 13:
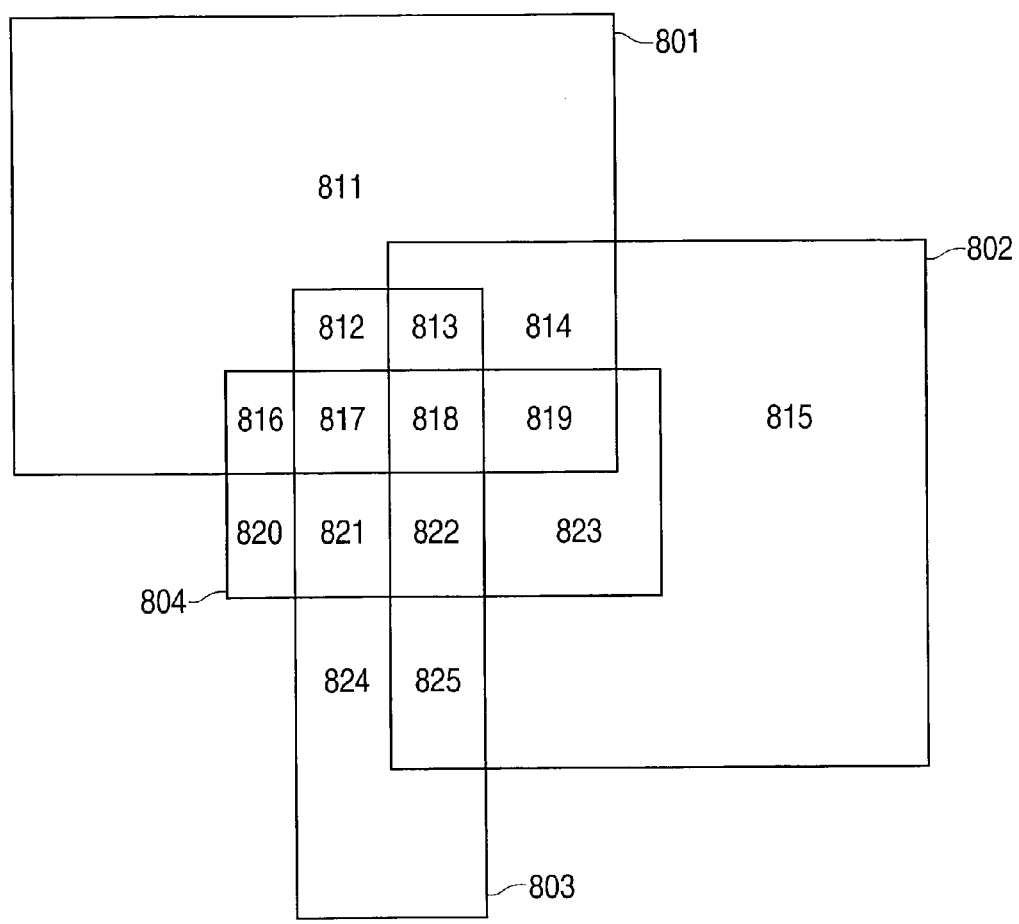
FIG. 13 illustrates a four-way overlap.

FIG. 13 depicts the overlap of four data sets or sectors 801–804 and the resulting 15 sub-sectors 811–825. The multiple overlap approach described herein provides the numbers of people represented in the 15 different sub-sectors represented in the diagram, and any of the combinations of sub-sectors (sectors). Again, the present invention can determine population estimates for all of the sub-sectors and overlaps between any of the sub-sectors.

The approach discussed previously herein measured the number of people represented in two data sets using a two-operation process. First, it determined the number of people necessary to increase the number of dates of birth, one increment at a time, from the largest of the original data sets to the combined data set. This number is then subtracted from the number of people represented in the smaller of the original two data sets. The remainder is the number of people shared by the two data sets.

Whitehead, A. N., & Russell, B. (1927). Principia Mathematica. Vol 1, 2nd Ed. Cambridge, University Press, 211–212 provide an alternative method of describing the overlap between two data sets using classical set theory.

$$(A \cap B) = A + B - (A \cup B)$$

In this conceptualization, the number of people who are shared by two data sets is the difference between the sum of the numbers of people represented in the two original data sets and the number of people represented in the combined data set. The size of the intersection of two sets ($A \cap B$) is the difference between the sum of the sizes of the two sets (A+B) and the size of the union of the two sets ($A \cup B$). The size of the two original data sets and the size of the combined data set are determined using the decomposition technique in the previously described herein. If B is the larger of the two original data sets, the quantity $(-(B-(A \cup B)))$ represents the number of people necessary to increase the number of dates of birth, one increment at a time, from the largest of the original data sets to the combined data set.

In the interest of simplicity, the procedure for determining three and more-way overlaps, the discussion that follows will use the notation of set theory, which, as shown above, obtaoms the sa,e resi;ts as the decomposition procedure described herein. The number of people represented in every one of three data sets is provided by the following formula.

$$(A \cap B \cap C) = A+B+C-(A \cup B)-(A \cup C)-(B \cup C)+(A \cup B \cup C)$$

The number of people in all three data sets is a function the number of people represented in each of the original data sets, in each of the pairs of the original data sets, and in the three data sets combined. Mathematically, it is possible to express overlap (intersection) problems as a function of size (union) problems using the mathematical inclusion/exclusion principle. The present invention provides valid and reliable estimates to the size problems that are involved in such computations.

To determine caseload overlap among multiple (N) data sets, multiple data sets are produced. In the case of three or more data sets the following procedure corresponds to or is similar to operation S130 of FIG. 3. The number of data sets is equal to $2^N-1$. These data sets are:

The N original data sets.
The $$\binom{N}{2}$$

(N-choose-two) data sets of all two-way concatenations.
The $$\binom{N}{3}$$

data sets of all three-way concatenations.

This process is continued through (N/N−1) data sets
The one data set that concatenates all N data sets.

Figure 14:
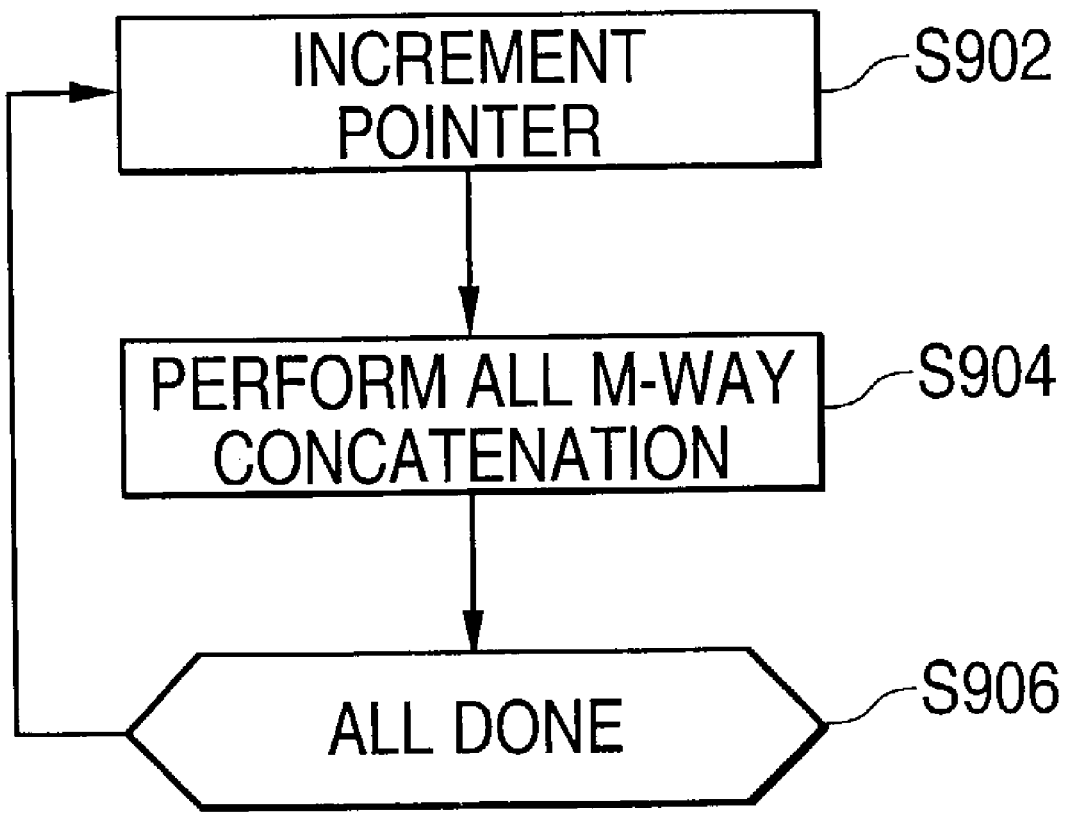
FIG. 14 depicts operations performed during overlap processing.

These operations are graphically shown in FIG. 14 and include incrementing S902 a concatenation pointer M and performing the concatenations S904 for all the M-way combinations. These concatenations are stored in the database (such as database 10 of FIG. 1). For example, a four-way overlap would create 15 data sets in the database. Then, the system determines S906 if all concatenations have been created ($M=2^N-1$?).

The decomposition algorithm previously discussed is applied to each of these data sets starting with S210 of FIG. 4. The results are used in various combinations to provide multiple data set caseload overlap parameters as desired.

A three-way procedure set forth in the Appendix I provides an example of the method used to determine the number of individuals represented in all three data sets, and in all possible combinations of the three data sets. These combinations of data sets include individuals represented in data sets 1 and 2 but not 3; individuals represented in data sets 1 but not 2 or 3; etc. In addition, the computer program provides an efficient method for determining the number of dates of birth within specific year-or-birth/gender cohorts for all potential data sets without physically creating data sets beyond the original three.

The three-way computer program tests for the presence of each date of birth in each year-or-birth/gender cohort in each of the original three (or more) data sets. It then determines, for each date of birth, whether or not it is represented in each year-or-birth/gender cohort in every possible combination of the original three (or more) data sets. The number of individuals represented in each of three (or more) original data sets is determined by the decomposition technique described in the original patent. The number of individuals represented in all possible combinations of the three (or more) original data sets is determined by the same technique.

A four-way procedure set forth in the Appendix I provides an example of the method used to determine the number of individuals represented in all four data sets, and in all possible combinations of four data sets.

Similar procedures for five-way, six-way, etc. overlaps can be provided by a person of skill in the art using the discussion herein and the procedures of the Appendix I as a guide. A person of skill in the art can also adapt the procedures of Appendix I for databases having different types of information, such as automobiles crossing a national border.

In obtaining estimates of the different intersections or sub-sectors of the overlapping data sets the multiple-overlap procedure essentially performs a union (or concatenation) operation-estimates and a linear combination. To determine an estimate for a particular sub-sector the invention determines estimates for the unions of data sets corresponding to the sub-sector and then linearly combines the union estimates to get an estimate for the sub-sector. For example, if the invention was trying to determine the population subsector 707 in FIG. 12, the invention would combine data sets MH, SA and CJ to get their union and determine population estimate for the union using the procedure discussed herein. The estimate of the union of these three sectors would then be added to estimates for MH, SA, and CJ individually. Three values are subtracted from this result. The value of the union of MH and SA, the value of the union of MH and CJ, and the value of the union of SA.

The multiple way decomposition technique particularly performs a cancellation of terms equivalent terms when one term is positive and another is negative. The smallest variance occurs when the fewest number of terms remain. This occurs when no terms are left to be cancelled.

The three and four way overlap procedures, as well as for higher numbers of overlaps, are an extension of the original two way overlap. They estimate unions of concatenated data sets, they use decomposition techniques to minimize variance by canceling terms, they produce 95% confidence intervals, and they address an important question relevant to program administrative and policy development.

The number of individuals represented in all the original data sets is determined using the procedures described above. The number of individuals represented in each of the possible sub-sets of the overlapping data sets is also determined using the procedures described above.

The multiple way overlap and size estimation procedure discussed herein can be performed in the hardware configuration of FIG. 1 or FIG. 9. If done in the web version, the remote customer computer would conduct all of the aggregation procedures The system also includes permanent or removable storage, such as magnetic and optical discs, RAM, ROM, etc. on which the process and data structures of the present invention can be stored and distributed. The processes can also be distributed via, for example, downloading over a network such as the Internet.

Furthermore, although a few preferred embodiments of the present invention have been described, it would be appreciated by those skilled in the art that changes may be made in these embodiments without departing from the principles and spirit of the invention, the scope of which is defined in the claims and their equivalents.

Appendix II

Diagnostic Procedure Output

**Diagnostic Procedures
for
PROBABILISTIC POPULATION ESTIMATION**

Probabilistic Population Estimation (PPE) of the unduplicated number of people represented in a data set (and shared across data sets) is based on four data elements: year, month, and day of birth and gender. If large numbers of records do not have legitimate values for these data elements, PPE will underestimate the number of people represented in the data set.

This first diagnostic procedure determines the number of records that do not have a legitimate year, month, or day of birth, or gender code. The frequency tables that follow report the number of records that do not have legitimate values for these data elements, individually and in combination.

In these tables, "Valid" denotes usable records, "Invalid" denotes records unusable because of invalid data values, and "Missing" denotes records unusable because of missing data.

In the DOB and Gender table, "Deleted Records" denotes the number of records excluded from PPE calculations. If more than 25% of records are deleted a warning will appear. Users may wish to investigated the reason for smaller numbers of missing records as well.

Frequency Table

Gender

|  |  | Frequency | Percent | Valid Percent | Cumulative Percent |
|---|---|---|---|---|---|
| Valid | Valid | 65194 | 100.0 | 100.0 | 100.0 |
|  | Missing | 1 | .0 | .0 | 100.0 |
|  | Total | 65195 | 100.0 | 100.0 |  |

Year of birth

|  |  | Frequency | Percent | Valid Percent | Cumulative Percent |
|---|---|---|---|---|---|
| Valid | Valid | 65194 | 100.0 | 100.0 | 100.0 |
|  | Invalid | 1 | .0 | .0 | 100.0 |
|  | Total | 65195 | 100.0 | 100.0 |  |

Month of birth

|  |  | Frequency | Percent | Valid Percent | Cumulative Percent |
|---|---|---|---|---|---|
| Valid | Valid | 65193 | 100.0 | 100.0 | 100.0 |
|  | Invalid | 2 | .0 | .0 | 100.0 |
|  | Total | 65195 | 100.0 | 100.0 |  |

Day of birth

|  |  | Frequency | Percent | Valid Percent | Cumulative Percent |
|---|---|---|---|---|---|
| Valid | Valid | 64716 | 99.3 | 99.3 | 99.3 |
|  | Invalid | 479 | .7 | .7 | 100.0 |
|  | Total | 65195 | 100.0 | 100.0 |  |

DOB

|  |  | Frequency | Percent | Valid Percent | Cumulative Percent |
|---|---|---|---|---|---|
| Valid | Valid DOB | 64713 | 99.3 | 99.3 | 99.3 |
|  | Invalid/missing | 482 | .7 | .7 | 100.0 |
|  | Total | 65195 | 100.0 | 100.0 |  |

DOB and Gender

|  |  | Frequency | Percent | Valid Percent | Cumulative Percent |
|---|---|---|---|---|---|
| Valid | Valid DOB and Gender | 64712 | 99.3 | 99.3 | 99.3 |
|  | Deleted records | 483 | .7 | .7 | 100.0 |
|  | Total | 65195 | 100.0 | 100.0 |  |

Probabiliatic Population Estimation assumes that the distribution of dates of birth in a data set reflects the distribution in the general population.

The following procedure compares the distributions of month and day of birth in the data set to the distributions in the general population and provides limits of acceptable variation in "effect size". The observed effect size should be between .5 and 2.0. If the observed variation exceeds these limits, the user should investigate the possibility of "administrative" dates of birth or other potential sources of irregularity.

Graph

Month of Birth

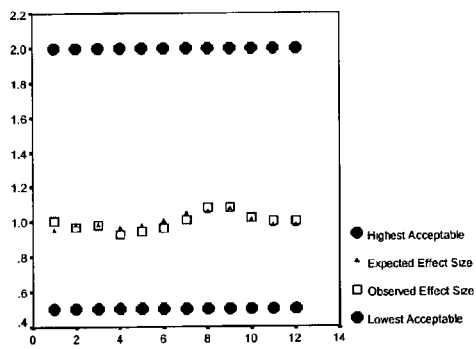

Summary for Birth Month

|  | Month | Observed Records | Expected Records | Observed Effect Size | Expected Effect Size |
|---|---|---|---|---|---|
| 1 | 1 | 5524 | 5492 | 1.01 | .95 |
| 2 | 2 | 4856 | 5005 | .97 | .98 |
| 3 | 3 | 5398 | 5492 | .98 | .98 |
| 4 | 4 | 4915 | 5315 | .92 | .96 |
| 5 | 5 | 5204 | 5492 | .95 | .97 |
| 6 | 6 | 5119 | 5315 | .96 | 1.00 |
| 7 | 7 | 5531 | 5492 | 1.01 | 1.05 |
| 8 | 8 | 5945 | 5492 | 1.08 | 1.06 |
| 9 | 9 | 5739 | 5315 | 1.08 | 1.07 |
| 10 | 10 | 5623 | 5492 | 1.02 | 1.01 |
| 11 | 11 | 5350 | 5315 | 1.01 | .98 |
| 12 | 12 | 5508 | 5492 | 1.00 | .98 |
| N | 12 | 12 | 12 | 12 | 12 |

Graph
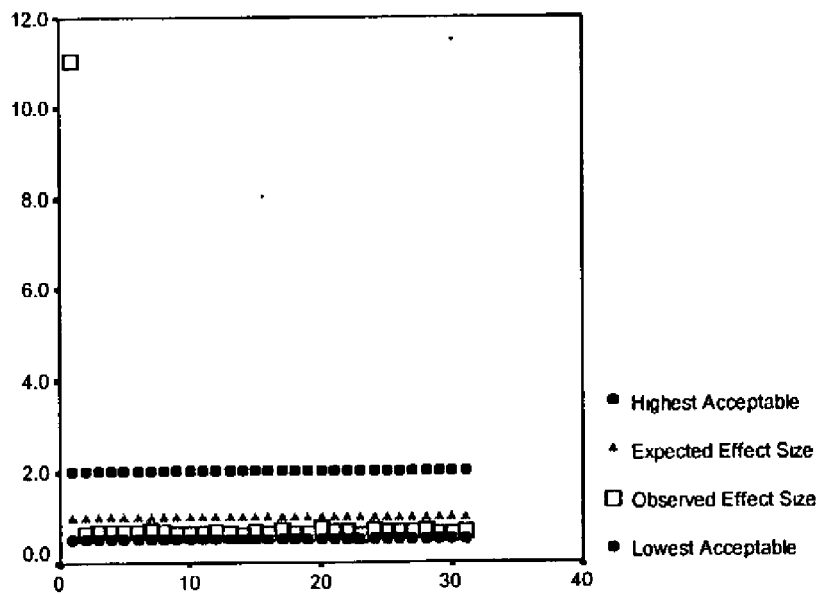
Day of Birth

Summary for Birth Day

|   | Day | Observed Records | Expected Records | Observed Effect Size | Expected Effect Size |
|---|---|---|---|---|---|
| 1 | 1 | 23535 | 2126 | 11.07 | 1.00 |
| 2 | 2 | 1352 | 2126 | .64 | 1.00 |
| 3 | 3 | 1386 | 2126 | .65 | 1.00 |
| 4 | 4 | 1390 | 2126 | .65 | 1.00 |
| 5 | 5 | 1424 | 2126 | .67 | 1.00 |
| 6 | 6 | 1399 | 2126 | .66 | 1.00 |
| 7 | 7 | 1487 | 2126 | .70 | 1.00 |
| 8 | 8 | 1424 | 2126 | .67 | 1.00 |
| 9 | 9 | 1318 | 2126 | .62 | 1.00 |
| 10 | 10 | 1374 | 2126 | .65 | 1.00 |
| 11 | 11 | 1342 | 2126 | .63 | 1.00 |
| 12 | 12 | 1403 | 2126 | .66 | 1.00 |
| 13 | 13 | 1341 | 2126 | .63 | 1.00 |
| 14 | 14 | 1292 | 2126 | .61 | 1.00 |
| 15 | 15 | 1415 | 2126 | .67 | 1.00 |
| 16 | 16 | 1364 | 2126 | .64 | 1.00 |
| 17 | 17 | 1518 | 2126 | .71 | 1.00 |
| 18 | 18 | 1332 | 2126 | .63 | 1.00 |
| 19 | 19 | 1355 | 2126 | .64 | 1.00 |
| 20 | 20 | 1592 | 2126 | .75 | 1.00 |
| 21 | 21 | 1421 | 2126 | .67 | 1.00 |
| 22 | 22 | 1451 | 2126 | .68 | 1.00 |
| 23 | 23 | 1232 | 2126 | .58 | 1.00 |
| 24 | 24 | 1489 | 2126 | .70 | 1.00 |
| 25 | 25 | 1425 | 2126 | .67 | 1.00 |
| 26 | 26 | 1407 | 2126 | .66 | 1.00 |
| 27 | 27 | 1422 | 2126 | .67 | 1.00 |
| 28 | 28 | 1471 | 2126 | .69 | 1.00 |
| 29 | 29 | 1239 | 1993 | .62 | 1.00 |
| 30 | 30 | 1260 | 1949 | .65 | 1.00 |
| 31 | 31 | 852 | 1240 | .69 | 1.00 |
| N | 31 | 31 | 31 | 31 | 31 |

| Day | Observed Records | Expected Records | Observed Effect Size | National Effect Size |
|---|---|---|---|---|
| 1 | 23535 | 2126 | 11.1 | 1.00 |

Warning : Assumption for distribution may not hold

The Observed Effect Size is Less than .5 or Greater than 2.0

Descriptives

Descriptive Statistics

|                   | N   | Maximum |
|-------------------|-----|---------|
| Days in a Cohort  | 157 | 317.00  |
| Valid N (listwise)| 157 |         |

—

The Diagnostic evaluation for this data set is complete

You received a Warning because the observed effect size for the following days exceeded the acceptable limits of variation

| Day | Observed Records | Expected Records | Observed Effect Size |
|-----|------------------|------------------|----------------------|
| 1   | 23535            | 2126             | 11.1                 |

What is claimed is:

1. A method of determining population size of unique entities in data, containing records on unique entities without unique identifiers for the unique entities, comprising:

receiving aggregate data comprising data set subset information and distribution occurrence information from a holder of the data; and determining a population size estimate from the aggregate data comprising performing decomposed probabilistic calculations based on values of the data with a known distribution.

2. A method of determining human population size and overlap of unique human individuals in data sets of a database held by a data holder, containing records on the unique human individuals without unique identifiers for the unique human individuals and having at least one common type of information with a known distribution of finite expectation comprising:

transferring a diagnostic procedure for performing error diagnosis on the data sets and an aggregate procedure for aggregating the data of the data sets;

diagnosing, by the holder, data record errors and omissions in the data sets using the diagnostic procedure; and creating, by the holder, a combined data set from the data sets of the data, determining whether the data is within a variance tolerance and determining the aggregate data from the data sets and the combined data set using the aggregate procedure, the aggregate data comprising data set subset information and distribution occurrence information;

transferring the aggregate data from the holder to an estimate processor;

determining, by the processor, a population size and data set overlap estimate from the aggregate data using decomposed probabilistic calculations based on values of the data with the known distribution; and transferring the size and overlap estimate from the processor to the holder.

3. A system for determining population size of unique entities in data, containing records on the unique entities without unique identifiers for the unique entities, comprising:

a data holder computer diagnosing data record errors in data sets of the data using a diagnostic procedure, creating a combined data set from the data sets of the data, determining aggregate data from the data sets and the combined data set, the aggregate data comprising data set subset and distribution occurrence information, and transmitting the aggregate data:

a communication facility carrying the aggregate data; and a estimate processor computer transmitting the diagnostic procedure and the aggregate procedure to the data holder computer via the communication facility, determining a population size and data set overlap estimate from the aggregate data and transferring the size and overlap estimate from the processor to the data holder computer.

* * * * *